US010426972B2

(12) United States Patent
Anderson

(10) Patent No.: US 10,426,972 B2
(45) Date of Patent: Oct. 1, 2019

(54) METHODS OF TREATING MELANOMA

(71) Applicant: Norman H. Anderson, Ocala, FL (US)

(72) Inventor: Norman H. Anderson, Ocala, FL (US)

(73) Assignee: MALIGNANT MELANOMA, LLC, Ocala, FL (US)

( * ) Notice: Subject to any disclaimer, the term of this patent is extended or adjusted under 35 U.S.C. 154(b) by 0 days.

(21) Appl. No.: 15/864,178

(22) Filed: Jan. 8, 2018

(65) Prior Publication Data
US 2018/0280724 A1    Oct. 4, 2018

Related U.S. Application Data

(62) Division of application No. 15/473,902, filed on Mar. 30, 2017, now Pat. No. 9,861,833.

(51) Int. Cl.
*A61N 5/10* (2006.01)
*A61K 45/06* (2006.01)

(52) U.S. Cl.
CPC ............... *A61N 5/10* (2013.01); *A61K 45/06* (2013.01); *A61N 2005/1087* (2013.01); *A61N 2005/1089* (2013.01)

(58) Field of Classification Search
CPC ...... A61N 5/10–1084; A61N 2005/1085–1098
See application file for complete search history.

(56) References Cited

PUBLICATIONS

Allen et al., "Acceleration of Hyperfractionated Chemoradiation Regimen for Advanced Head and Neck Cancer," Head Neck., vol. 29, No. 2, p. 137-142, 2007. (Year: 2007).*
Gupta et al., "Early Clinical Outcomes Demonstrate Preserved Cognitive Function in Children with Average-Risk Medulloblastoma When Treated with Hyperfractionated Radiation Therapy," Int. J. Radiation Oncol. Biol. Phys., vol. 83, No. 5, p. 1534-1540, 2012. (Year: 2012).*
Hayden et al., "Hyperfractionated External Beam Radiation Therapy in the Treatment of MurineTransgenic Retinoblastoma," Arch. Ophthalmol., vol. 120, p. 353-359, 2002. (Year: 2002).*
Chang, D. T. et al. "Adjuvant Radiotherapy for Cutaneous Melanoma: Comparing Hypofractionation to Conventional Fractionation" Int. J. Radiation Oncology Biol. Phys., 2006, pp. 1051-1055, vol. 66, No. 4.

(Continued)

*Primary Examiner* — Thaddeus B Cox
(74) *Attorney, Agent, or Firm* — Saliwanchik, Lloyd & Eisenschenk

(57) ABSTRACT

The present disclosure is directed to methods of treating malignant melanoma by irradiating sites to which melanoma cells have become locally advanced, surgically undesirable, or have metastasized. In various embodiments of the invention, patients are treated with radiation doses in amounts ranging from about 25 to 230 cGy, preferably about 100 cGy to about 200 cGy, at least twice a day. The treatment regimen can be performed in the absence of additional treatments for the metastatic melanoma (e.g., chemotherapy/targeted therapy/immunotherapy) or in combination with additional therapies for chemotherapy/targeted therapy/immunotherapy. Various additional embodiments relate to the administration of between 20 and 100 fractions of radiation, preferably between 20 and 56 fractions of radiation.

19 Claims, 59 Drawing Sheets
(52 of 59 Drawing Sheet(s) Filed in Color)

(56) References Cited

PUBLICATIONS

Choi, K. N. et al. "Intracranial Metastases from Melanoma—Clinical Features and Treatment by Accelerated Fractionation" *Cancer*, Jul. 1, 1985, pp. 1-9, vol. 56, No. 1.

Graham, P. H. et al. "Randomized Comparison of Whole Brain Radiotherapy, 20 GY in Four Daily Fractions Versus 40 GY in 20 Twice-Daily Fractions, for Brain Metastases" *Int. J. Radiation Oncology Biol. Phys.*, 2010, pp. 648-654, vol. 77, No. 3.

Kubicek, G. J. et al. "Adjuvant Radiation for Malignant Melanoma: The KUMC Experience" *Kansas Journal of Medicine*, 2008, pp. 1-7.

Magnuson, W. J. et al. "Successful Treatment of Melanoma Metastatic to the Left Atrium Using External Beam Radiation Therapy" *Oncology*, Jun. 15, 2010, pp. 1-6.

Mahadevan, A. et al. "Radiation Therapy in the Management of Malignant Melanoma" *Oncology*, Oct. 15, 2015, pp. 1-13.

Pudelek, K. et al. "Radiotherapy of malignant melanoma cerebral metastases—results of treatment" *Nowotowory Journal of Oncology*, 2004, pp. 28-30, vol. 54, No. 1.

Sause, W. T. "Phase I/II Trial of Accelerated Fractionation in Brain Metastases RTOG 85-28" *Int. J. Radiation Oncology Biol. Phys.*, 1993, pp. 653-657, vol. 26.

Sharpe, M. et al. "Genetically modified T cells in cancer therapy: opportunities and challenges" *Disease Models and Mechanisms*, 2015, pp. 337-350, vol. 8.

Applicant statement dated Jul. 26, 2017, p. 1.

Rofstad, E. K. "Radiation Biology of Malignant Melanoma" *Acta Radiologica: Oncology*, 1986, pp. 1-10, vol. 25, No. 1.

Bentzen, S. M. et al. "Clinical radiobiology of malignant melanoma" *Radiotherapy and Oncology*, 1989, pp. 169-182, vol. 16.

OzRadOnc "Clinical Use of the a/β Ratio" retrieved on Jan. 5, 2018, retrieved from the internet, URL: http://ozradonc.wikidot.com/clinical-use-of-the-alpha-beta-ratio, pp. 1-2.

Jahanshahi, P. et al. "Malignant melanoma and radiotherapy: past myths, excellent local control in 146 studied lesions at Georgetown University, and improving future management" *Frontiers in Oncology*, Nov. 15, 2012, pp. 1-6, vol. 2, No. 167.

Khan, N. et al. "The Evolving Role of Radiation Therapy in the Management of Malignant Melanoma" *Int J Radiat Oncol Biol Phys*, Jul. 1, 2011, pp. 1-17, vol. 80, No. 3.

Khan, M. K. et al. "Future of radiation therapy for malignant melanoma in an era of newer, more effective biological agents" *OncoTargets and Therapy*, Aug. 8, 2011, pp. 137-148, vol. 4.

Kim, M.-S. et al. "Radiobiological mechanisms of stereotactic body radiation therapy and stereotactic radiation surgery" *Radiation Oncology Journal*, 2015, pp. 265-275, vol. 33, No. 4.

Mahadevan, A. et al. "Radiation Therapy in the Management of Malignant Melanoma" *Cancer Network*, Oct. 15, 2015, pp. 1-13.

Overgaard, J. et al. "Some factors of importance in the radiation treatment of malignant melanoma" *Radiotherapy Oncology*, Mar. 1986, p. 1, vol. 5, No. 3, Abstract Only.

Shiao, S. L. et al. "Radiation and Melanoma: A Phoenix Rising" *The American Journal of Hematology/Oncology*, 2017, pp. 39-41, vol. 11, No. 2.

Skowronek, J. et al. "The Role of Radiotherapy in the Treatment of Malignant Melanoma" *Rep. Pract. Oncolo. Radiother.*, 1998, pp. 1-5, vol. 3, No. 1.

Strojan, P. "Role of radiotherapy in melanoma management" *Radiology and Oncology*, Mar. 18, 2010, pp. 1-12, vol. 44, No. 1.

Trott, K.-R. "The Optimal Radiation Dose Per Fraction for the Treatment of Malignant Melanomas" *Int J. Radiation Oncology Biol. Phys.*, Apr. 1991, pp. 905-907, vol. 20, No. 4.

Wazer, D. E. "Role of radiation therapy in the management of melanoma" UpToDate.com, 2011, pp. 1-17.

\* cited by examiner

Keynote 029: AE Summary

| Category | Treatment Related N = 153 | Immune Mediated[a] N = 153 |
|---|---|---|
| Any grade | 145 (95%) | 89 (58%) |
| Grade 3-4 | 64 (42%) | 38 (25%) |
| Led to death | 0 | 0 |
| Led to ipilimumab discontinuation only | 16 (10%) | 12 (8%) |
| Led to pembrolizumab discontinuation[b] | 11 (7%) | 6 (4%) |
| Led to ipilimumab and pembrolizumab discontinuation[c] | 16 (10%) | 11 (7%) |

[a] Includes 13 patients with prior BRAF ± MEK inhibitor therapy.

[b] 2 patients had tumors not evaluable for PD-L1 expression. Positivity was defined as ≥1% staining in tumor and adjacent immune cells as assessed by IHC (22C3 antibody). Data cutoff date: March 17, 2016.

Figure 1

MAY 23, 2016
SEPTEMBER 27, 2016
Figure 16

June 11, 2014

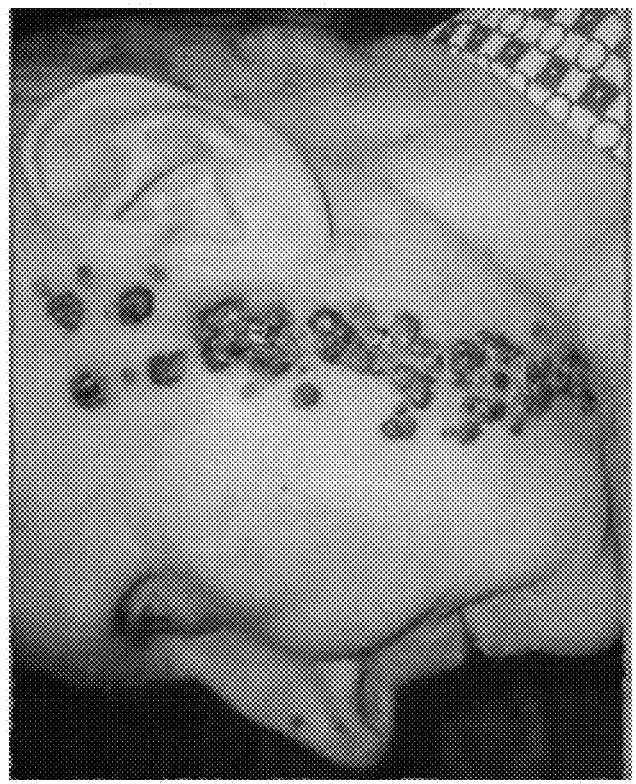
Figure 37

METHODS OF TREATING MELANOMA

CROSS-REFERENCE TO RELATED APPLICATION

This application is a divisional of U.S. application Ser. No. 15/473,902, filed Mar. 30, 2017, now U.S. Pat. No. 9,861,833.

BACKGROUND OF THE INVENTION

Skin cancer is the most common form of cancer in the U.S., with more than 3.5 million skin cancers diagnosed annually. There are three major types of skin cancer: (1) basal cell carcinoma; (2) squamous cell carcinoma; and (3) melanoma. Of these three forms of skin cancer, melanoma is the deadliest form of the disease.

Basal cell carcinoma is the most common type of skin cancer in humans. These cancers tend to grow slowly and rarely spread to nearby lymph nodes or to distant parts of the body (see Worldwide Website: cancer.org). Treatment methods include simple excision, radiation therapy, and chemotherapy, among others (see Worldwide Website: cancer.org).

Squamous cell carcinoma grows and spreads more than basal cell cancers. This cancer is more likely to invade fatty tissues just beneath the skin and is more likely to spread to lymph nodes and/or distant parts of the body, although this is still uncommon (see Worldwide Website: cancer.org). Treatment methods include excision, radiation therapy, systemic chemotherapy, and lymph node dissection (see Worldwide Website: cancer.org).

Malignant melanoma is a highly aggressive, chemo-resistant, radio-resistant and lethal malignant neoplasm which is responsible for 60-80% mortality among all skin cancers, with a 5 year survival rate of 14%. 2% of the population will be diagnosed with this malignancy, and well over 10,000 will die this year in the United States alone from metastatic melanoma. After melanoma has been diagnosed, there are five standard types of treatment used: surgery, chemotherapy, biologic therapy, targeted therapy, and radiation therapy. Surgical excisions are an early treatment method utilized for patients with thin, non-invasive lesions; excisional biopsies are conducted for easy histological evaluation and assessing excision margins of the remaining tumor. Melanoma has a high potential for systemic metastasis.

Historical Approach to Radiation Delivery

The historical precedent for delivering radiation therapy is to deliver treatment once daily; however, the application of twice-daily radiation therapy began over 40 years ago and was applied to the treatment of head and neck malignancies. Squamous cell carcinomas of the head and neck region respond well to radiation. It was believed that if the dose-per-fraction of radiation was reduced and the delivery of treatment occurred twice-daily rather than once, such an approach may provide therapeutic advantage. The theory is based upon the sigmoid-response curve and is well known in radiobiology. An improvement in local/regional control for head and neck cancers was provided in several studies. At the same time, less morbidity was experienced to a patient's uninvolved but exposed tissue. Despite the objective success, the utilization of twice-daily treatment for head and neck malignancies seldom if ever occurs, and its application has not been expanded to other malignancies. Factors cited for the discontinuation of twice-daily treatment include inconvenience to patients.

A program of using twice-daily radiation for advanced ovarian carcinomas was used in the mid-1980's. Ovarian malignant cells were known to respond favorably to radiation. However, the change in dose administered per fraction was lowered, the emphasis being to safely protect a vast region of "at risk/exposed" normal tissue. The overall results proved beneficial, as length of survival was extended for these patients. Chemotherapy, as it evolved, replaced this approach, due to the nature of how ovarian cancer spreads.

Twice-daily radiation therapy was used in 1985 for advanced brain malignancies, which were also known to respond to radiation. Although improvement in survival occurs with radiation, the issue with this malignancy is one of local failure rather than spread. This sets the initial application for twice-daily treatment to provide increased local/regional control and decreased side effects to normal tissue for malignancies that characteristically are not blood-borne, but rather spread by direct or lymphatic extension. Theories attribute these results to either a genetic or metabolic effect of ionizing radiation. The benefit is only seen as a local response, and is based upon the assumption that increasing the total dose administered results in an increase in local control for those malignancies known to be sensitive to radiation.

This assumption is applied to both the principles of radiation delivery and the use of chemotherapy/immunotherapy. Current understanding of a malignant cell's response applies similarly for the use of either once-daily or twice-daily treatment for the above-mentioned cancer types. Although previously used for some solid lung malignancies shown to have a positive response to radiation and whose tolerance of normal tissue is lacking, the examples cited above are furnished to establish and emphasize the safety of this treatment approach to normal tissue. Safety to normal tissue has been the basis for its very rare and incidental use in the past. The vast majority of radiation oncologists and virtually none of the more recently-trained oncologists have ever used a twice-daily treatment technique.

However, one specific malignancy, i.e. malignant melanoma, is known to be "radiation resistant" when the treatment involves the standard doses used for once-daily administration. The lack of clinical benefit has been documented in the medical literature for more than half a century. During 1980s, it was understood that, albeit for microscopic post-operative disease, radiation was an ineffective treatment for malignant melanoma because, as research substantiated, radiation did not provide any level of tumor control. This belief has been promulgated and fixed in the medical literature. Repeated to every resident in their training, radiation is ineffective for this particular malignancy. Radiation is seldom listed in any protocol, publication or by any national melanoma association as a treatment option and has not in the recent past been mentioned in the National Comprehensive Cancer Network (NCCN) guidelines. An upcoming academic melanoma and cutaneous malignancy conference is to be held in New York City on Mar. 24-25, 2017. Of 22 university speakers, none are radiation oncologists, and there are no presentations for radiation therapy in the treatment for melanomas. The unalterable medical assumption would be its lack of effectiveness with any single-daily dose schedule, since that delivery has proved to be ineffective.

The more recent approach toward the treatment of this malignancy, in particular for its regional spread/involvement, is to increase the amount of energy given with the once-daily dose per fraction of radiation, but administer treatment in fewer fractions (a hypofractionated regimen). This has appeared to result in slightly increased local/regional control within the treated area of the malignancy. However, no study has shown any improvement in long-term survival with such an approach. The most recent utilization of either targeted or immunotherapy combined with high dose-per-fraction radiation (hypofractionation) has resulted in improved but incomplete local/regional control, with slight improvement for overall time of survival. However, the morbidity to normal tissue with such an approach is significant, as illustrated by the radiobiologic sigmoid-response curve, and severely limits its practical application. The intensity of side effects can prove fatal. There becomes a trade off as to whether this recent treatment plan's effectiveness, albeit incomplete in response and not curative, is offset by the resultant loss of quality of life. However, it is the only approach presently known, utilized, and viewed as a viable alternative.

Further, if the use of standard once-daily treatment has been discredited over half a century, the idea of "weaker doses" administered with each treatment would defy any logic for using twice-daily radiation. Specifically, if once-daily treatment is ineffective, as extensively documented, the assumption is logical that this particular malignancy has proven to be radiation "resistant," and must require large doses at each once-daily administration. Lower dose in twice-daily or multi-daily radiation were never considered and, indeed, would be formally rejected.

In essence, with the universal opposition to a standard radiation fractionation for the treatment of this particular malignancy, the steady push has been to escalate the dose for each treatment, administered once-daily, completed in very few treatment fractions. Further, documentation in the medical literature cannot be found that refers to twice-daily administration for malignant melanoma.

A Local/Regional Response

The spread of head and neck malignancies is almost never blood-borne and is rather by direct extension or by lymphatic spread. The response seen with head and neck malignancies is more of a metabolic response to treatment rather than immunologic and this response differs markedly from the protocol described in the instant invention. The previous emphasis of using twice-daily treatment is to increase local/regional control of head and neck cancer, while reducing damage to normal tissue. The effect is limited to the area of treatment, because that is the only region addressed with radiation as a focused approach.

Similar doses of radiation therapy applied to malignant melanoma, historically administered once daily at 180 cGy to 230 cGy per fraction, resulted in minimal local/regional control. Thus, its clinical application in the past has only been used for that of microscopic residual malignant melanoma disease, normally following a surgical resection of the primary cancer. Radiation has not been used effectively for metastatic disease other than with hypo-fractionated regimens referred to previously, where doses in excess of 300 cGy (routinely 500 cGy to 1,000 cGy, i.e. 950 cGy times 3 fractions over seven days or 2,000 cGy delivered in one fraction) are administered once-daily. Doses of radiation in this range result in increased morbidity (the greater the dose with each administration, the greater the morbidity to normal tissue). Delivered without immunotherapy, these doses provide no difference in long-term survival, and with immunotherapy, they provide a slight improvement in long-term survival.

A Total Body Immune Response

There is no obvious part of the immune system that is activated by the treatment of those malignancies whose spread pattern is by either direct extension or lymphatic in nature, possibly due to the low presence of dendritic cells. Twice-daily treatment was rarely, if ever, attempted in the past to reduce collateral damage and protect vital body organs. The sophistication of recent computerized (and expensive) treatment technology similarly reduces dosage to uninvolved tissue by using complex, multi-beam design for radiation delivery, essentially minimizing adverse impact by spreading exposure over a dispersed area. Although the impact to normal tissue may be similar with either approach, more complex technology encourages shorter courses to be administered, eliminating any remaining role for twice-daily treatment. Advanced technology moves in the direction of reducing the number of treatments, each delivered in larger amounts, because its delivery can spare adverse effects to normal tissue. This is well documented in the medical literature. Further, if a patient faces short-term survival, even exceeding normal tissue tolerance is justified because the normal organs would not exist to experience long term morbidity, thus further diverging the application of radiation toward a limited number of treatments.

By adhering to the disclosed radiation protocol, treatment of malignant melanoma can be effectively delivered at approximately 5% of the present annual health care cost compared to pharmaceutical agents. Also, unlike present pharmaceutical agents, markedly increased local/regional control and a potential cure can be achieved. The drug regimens presently available are up to 200 times more expensive for a year's intervention and require frequent hospitalizations for adverse drug-induced side effects, are temporary as to benefit, and every patient to date eventually progresses with disease.

One of the most utilized immunotherapeutic drugs, Keytruda, is recommended at a dose of up to 10 mg/kg. Based upon the average patient's size, the present cost for Keytruda is as much as $83,000 monthly. The drug would, unless stopped due to toxicity, be routinely continued until progression of disease occurs. If that time frame is 12 months, the cost may be greater than $1 million per patient, excluding the required hospitalizations for untoward sequelae.

A recent study to treat metastatic malignant melanoma (Keynote 029) utilized a combination of a PDL-1 antibody in the form of Yervoy and Cytotoxic T-lymphocyte associated antigen-4 antibody in the form of Keytruda. The results were reported at the recent annual ASCO meeting. Toxicity is graded from I to IV. I is mildest, and requires no interruption in the administration of treatment. Grade II is moderate, and requires a temporary interruption in treatment administration. Grades III and IV are severe and life-threatening respectively, and, according to national guidelines, require the termination of the drug from further use.

FIG. 1 provides a slide presented at the ASCO Annual Meeting 2016 by Dr. G. V. Long, Keynote 029: AE. As FIG. 1 indicates, Grade III and IV toxicity occurred in 67% of patients when treatment related and immune related adverse events are combined. In essence ⅔ of patients experienced severe and life-threatening toxicity from combination drug therapy. As the table above indicates, discontinuation of either or both drugs involved 46% of patients.

This compares to, at most, Grade I toxicity with radiation, administered twice daily depending on multiple factors, including the area of the body treated and the extent of the radiation-induced immune-related effect (normally symptoms of the flu). In essence, toxicity from radiation is rare. When one factors in potential hospitalization for Grade III and IV toxicity, the cost resulting from pharmaceutical immunotherapy to include financial, physical, and emotional can be devastating. This makes radiation treatment a more cost effective when delivered in a twice daily protocol and a far more physiologically tolerable treatment regimen for malignant melanoma. Accordingly, the disclosed invention seeks to provide treatment of malignant melanoma in a more cost effective way and with significantly lower incidence of adverse physiological and psychological events.

BRIEF SUMMARY OF THE INVENTION

The invention provides a method for treating malignant melanoma comprising the use of radiation therapy in which a dose of about 25 to about 230 centiGray (cGy), preferably about 100 to about 200 cGy, of radiation is delivered to a site of locally advanced or metastasized malignant melanoma. Radiation therapy is administered at least twice per day to the subject.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1 provides a slide presented at the ASCO Annual Meeting 2016 by Dr. G. V. Long, Keynote 029: AE.

FIGS. 15 and 16 represent serial PET/CT scans, including the original as well as follow-up scans, for the patient of Example 4.

FIGS. 18-37 illustrate disease progression for the patient of Example 6, including the appearance at the time of initial evaluation.

DETAILED DESCRIPTION OF THE INVENTION

Figure 2:
FIG. 2 shows an MRI of the brain.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range of 0-20%, 0 to 10%, 0 to 5%, or up to 1% of a given value. Where particular values are described in the application and claims, the terms "about" or "approximately" are used and provide for a variation of 0-10% around the value (X±10%). In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned; for example, a range of 5-10 indicates all the values between 5.0 and 10.0 as well as between 5.00 and 10.00, including the terminal values.

"Treatment", "treating", "palliating" and "ameliorating" (and grammatical variants of these terms), as used herein, are used interchangeably. These terms refer to an approach for obtaining beneficial or desired results including, but not limited to, therapeutic benefit. A therapeutic benefit is achieved with the eradication or amelioration of one or more of the physiological symptoms associated with the underlying disorder, such that an improvement is observed in the patient, notwithstanding that the patient may still be afflicted with the underlying disorder.

The term "effective amount" or "therapeutically effective amount" refers to that amount of a radiation, as described herein, that is sufficient to effect a therapeutic benefit to a subject. The therapeutically effective amount may vary depending upon the intended subject and disease condition with respect to treating malignant melanoma, e.g., the weight and age of the subject, the severity of disease, the manner of administration and the like, which can readily be determined by one of ordinary skill in the art.

The term "subject" refers to an animal, such as a mammal, for example a human. The methods described herein can be useful in both humans and non-human animals. In some embodiments, the subject is a mammal (such as an animal model of disease), and in some embodiments, the subject is human. The terms "subject" and "patient" can be used interchangeably.

The term "centiGray (cGy)" as used herein refers to a derived metric (SI) measurement unit of absorbed radiation dose of ionizing radiation, e.g. x-rays. The SI prefix centi stands for one hundredths. The centiGray is equal to one hundredth of a gray (0.01 Gy), and the gray is defined as the absorption of one joule of ionizing radiation by one kilogram (1 J/kg) of matter, e.g., human tissue.

Thus, the described invention provides methods for treating a locally advanced, surgically undesirable, or metastatic malignant melanoma in a subject administering radiation therapy in a dose (fraction) of about 25-230 centiGray (cGy), preferably about 100-200 centiGray (cGy), at a site to which melanoma has locally invaded or metastasized. Radiation therapy is provided to the subject with radiation being administered over at least two doses (fractions) per day. For example, fractions of radiation therapy can be administered from two (2) to ten (10) times per day with an interval of at least about one hour between fractions of radiation. In such a situation, between 2 and 11 fractions of radiation can be administered to a subject per day. Typically, between 2 and 6 fractions of radiation are administered to a subject each day. In certain preferred embodiments, two (2) fractions of radiation are administered to a subject per day. In certain aspects of the invention, a total of between with a total of between 20 and 100 fractions of radiation can be administered to a subject. Some embodiments contemplate treating a subject with a total of between 20 and 56 fractions of radiation.

As would be apparent to those skilled in the art, the interval between fractions is dependent upon the number of fractions of radiation being administered to a subject each day. Thus where two fractions of radiation in doses of about 100-200 cGy are administered, one can have an interval of between about 1 hour and, maximally, about 23 hours. However, typical intervals between radiation fractions are between about 2 hours and about 10 hours, more preferably between about 2 hours and about 8 hours or between about 2 hours and about 6 hours.

Certain embodiments of the invention provide a twice-daily approach for the treatment of locally advanced/regional/metastatic malignant melanoma. This approach causes a biologically different and unpredictable response from the cancer cells. The dose-per-fraction regimen and its schedule of delivery specified herein, with documentation for twice-daily treatment, change both the understanding of what takes place and what the required total dose really is as applied to malignant melanoma. The biologic sensitivity of a malignant melanoma cell with this different and previously unrealized approach is somehow modified, requiring less of a total dose to be administered, while at the same time achieving a marked increase in local/regional control. In essence, local/regional control of disease has exceeded 95%. Locally invasive and/or regional disease of any mass size responds with complete disappearance in many patients. This now provides an increased time for survival well beyond what is presently offered and with a previously unseen potential for cure. The invention reveals beneficial results beyond the treatment of local/regional spread to include regression of untreated distant metastatic malignant melanoma affecting organs/tissue, as documented both clinically and radiographically, without the use of any pharmaceutical agent.

The described invention contemplates the treatment of malignant melanoma patients using the disclosed radiation therapy either alone or in combination with other treatments for malignant melanoma. Non-limiting examples of such added treatments include surgery (e.g., wide excision surgery), chemotherapy (e.g., treatment with vemurafenib, dabrafenib, trametinib, cobimetinib, temozolomide, dacarbazine, paclitaxel, etc.) or immunotherapy (e.g., pembrolizumab, ipilmumab, nivolumab, interfereon alpha, interferon alpha 2b).

The following are guidelines for administering the radiation therapy according to the invention described herein. The dose per fraction to be delivered includes a dose range from 25 cGy per-fraction to 230 cGy per-fraction, delivered up to seven times daily, for the treatment of local, regional, or metastatic malignant melanoma. The total dose administered for the entire course of treatment to a certain area of the body will vary and is to be defined by the amount of radiation delivered with each fraction, the number of fractions (two or more) delivered daily, as well as the volume of tissue exposed to treatment. Total dose recommendations can be adjusted as needed. The larger the volume requiring treatment, the less dose of radiation per fraction that can safely be administered. For example, higher doses of radiation administered with each fraction require less of a total dose. However, these doses are carefully adjusted based upon the normal tissue exposed to radiation. This varies dramatically from one area/organ of the body to another and doses are adjusted based upon the nature of that specific organ structure(s) exposed as well as the volume of tissue exposed to radiation, ultimately leading to the total dose received. As a result, this approach dramatically reduces side effects to normal tissue both during treatment and, more importantly, long-term. The range of ideal dosing and scheduling of its delivery is provided herein and can be modified on a case by case basis within the realm of the guidelines provided herein.

The radiation guidelines presented herein cause devastating effect on malignant melanoma and also provide secondary protective effect on normal tissue. The fact that the elimination of malignant melanoma occurs under this design, while still very much considering the tolerance of the surrounding organ tissue, raises variables essential to its success. These variables include the dramatic local/regional control, unexplained in the conventional understanding, as well as a potential total body immune response without the aid of drugs. The invention establishes an untapped uniqueness of treatment design which has never been realized for this particular malignancy.

The application also provides the following non-limiting embodiments:

1. A method for treating malignant melanoma in a subject comprising irradiating malignant melanoma within the subject with at least two fractions of radiation per day, said fractions of radiation being between about 25 to about 230 centiGray (cGy), preferably about 100 to about 200 centiGray (cGy), and said fractions being separated by a time interval of at least about 0.5 hour.

2. The method according to embodiment 1, wherein the fractions of radiation are separated by a time interval ranging from about 1 hour and, maximally, about 23 hours.

3. The method according to embodiment 1, wherein the fractions of radiation are separated by a time interval ranging from about 1 hours and about 8 hours.

4. The method according to embodiment 1, wherein the fractions of radiation are separated by a time interval ranging from about 2 hours and about 8 hours.

5. The method according to embodiment 1, wherein the fractions of radiation are separated by a time interval ranging from about 1 hours and about 6 hours.

6. The method according to any one of embodiments 1-5, said method comprising treating said subject with radiation and a therapy comprising surgery, chemotherapy, immunotherapy or a combination of said therapies.

7. The method according to embodiment 6, wherein said chemotherapy/targeted therapy/immunotherapy is selected from treatment with vemurafenib, dabrafenib, trametinib, cobimetinib, temozolomide, dacarbazine, paclitaxel or combinations thereof.

8. The method according to embodiment 6, wherein said chemotherapy/targeted therapy/immunotherapy is selected from treatment with pembrolizumab, ipilmumab, nivolumab, interfereon alpha, interferon alpha 2b or combinations thereof.

9. The method according to any one of embodiments 1-5, wherein said subject is treated with a total of between 20 and 100 fractions of radiation.

10. The method according to embodiment 9, wherein said subject is treated with a total of between 20 and 56 fractions of radiation.

11. The method according to embodiment 6, wherein said subject is treated with a total of between 20 and 100 fractions of radiation.

12. The method according to embodiment 11, wherein said subject is treated with a total of between 20 and 56 fractions of radiation.

13. The method according to embodiment 7, wherein said subject is treated with a total of between 20 and 100 fractions of radiation.

14. The method according to embodiment 13, wherein said subject is treated with a total of between 20 and 56 fractions of radiation.

15. The method according to embodiment 8, wherein said subject is treated with a total of between 20 and 100 fractions of radiation.

16. The method according to embodiment 15, wherein said subject is treated with a total of between 20 and 56 fractions of radiation.

Materials and Methods

Not limited to the type of equipment or type of energy used, i.e., whether it be photon, electron, orthovoltage, or proton beam. Not limited to the design of treatment, i.e., simple appositional, parallel opposed, multi-field conventional, IMRT, or other forms of design. The type of equipment and design of the treatment represents the state of technology. There will be no change in these factors.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example One

Figure 3:
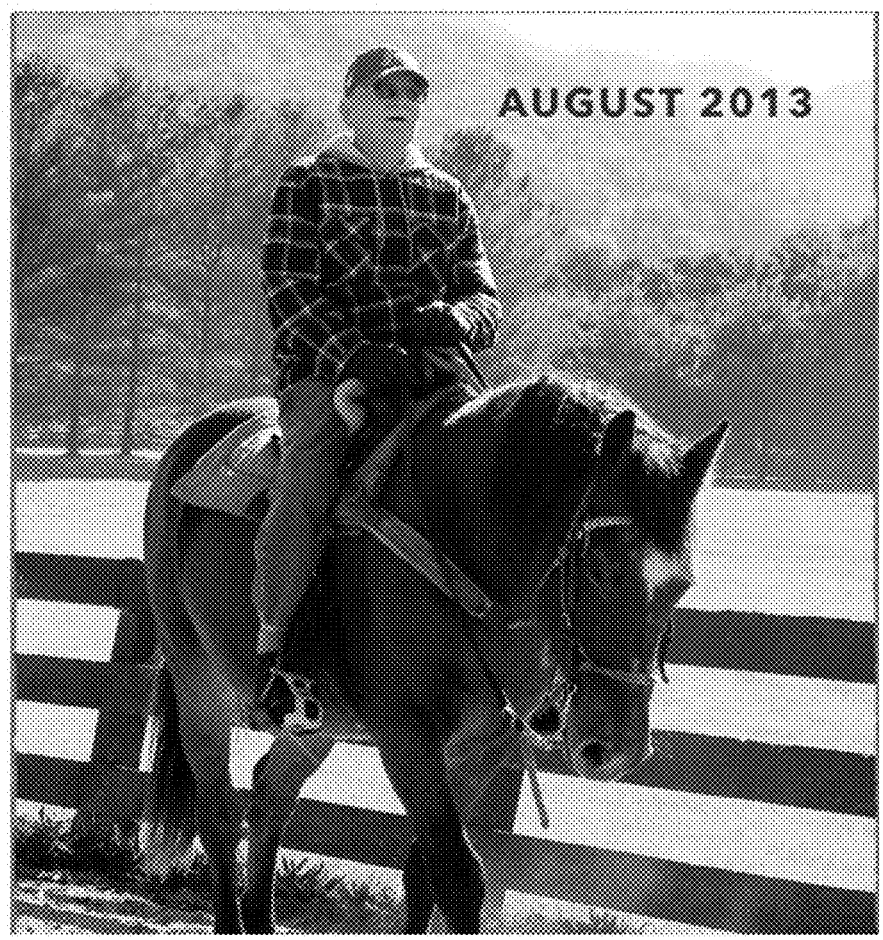
FIG. 3 shows a patient resuming normal activity.

An MRI of the brain was performed (FIG. 2) for this symptomatic gentleman with a history of confirmed malignant melanoma. The study demonstrated a 3.7×3.6×3.0 cm enhancing mass lesion in the left frontal lobe of the brain, with surrounding swelling. There was a shift of the midline structures to the contralateral right side. Symptoms of nausea and vomiting forced the patient to remain immobile. He was found not to be a surgical candidate. 6 MV photon radiation was administered for about one month, delivering 5940 cGy at 135 cGy per fraction, twice-daily. No systemic intervention was ever administered. (FIG. 3) The patient was subsequently able to resume normal activity, such as horseback riding, within three to four months after treatment.

Figure 4:
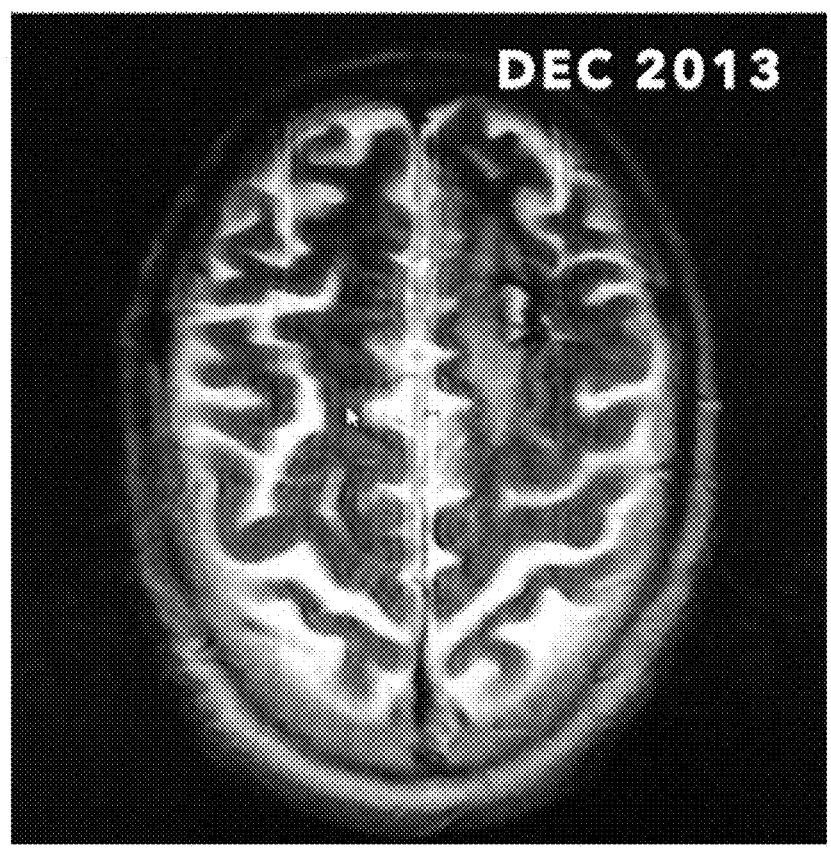
FIG. 4 shows a repeat MM of the patient of FIGS. 1 and 2 (the patient of Example 1).

A repeat Mill (FIG. 4) demonstrated a residual 1.0 cm calcification with slight surrounding edema. There was no activity following the administration of gadolinium, indicating there was no cancer evident on this study. He remained asymptomatic thereafter.

Example Two

A 68-year-old gentleman presented with a 1.6 mm Clark level IV malignant melanoma involving the skin of the right back. The Moffitt Cancer Center in Tampa, Fla. performed intra-operative lymphatic mapping, sentinel node biopsy of the right axilla, radical wide local excision, and flap advancement, with four negative sentinel nodes.

Figure 5:
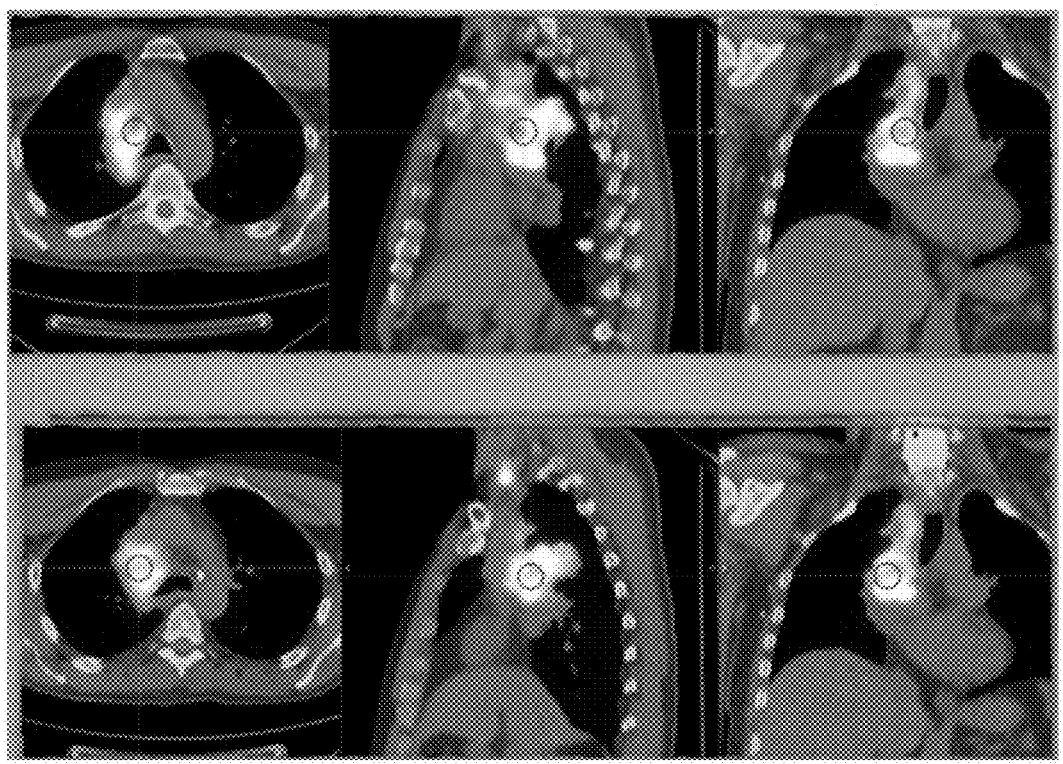
FIG. 5. Symptoms of respiratory distress led to a CT scan demonstrating a 5×6 cm right suprahilar/paramediastinal mass, with deviation of the trachea and ascending aorta as well as subcarinal adenopathy.

Symptoms of respiratory distress led to a CT scan demonstrating a 5×6 cm right suprahilar/paramediastinal mass, with deviation of the trachea and ascending aorta as well as subcarinal adenopathy. A PET/CT demonstrated a "massive" hypermetabolic mass within the mid-chest with highly elevated metabolic activity of 22 units, involving the paratracheal, hilar, and subcarinal space (FIG. 5).

Figure 6:
FIG. 6 shows inflammatory changes due to treatment.
Figure 7:
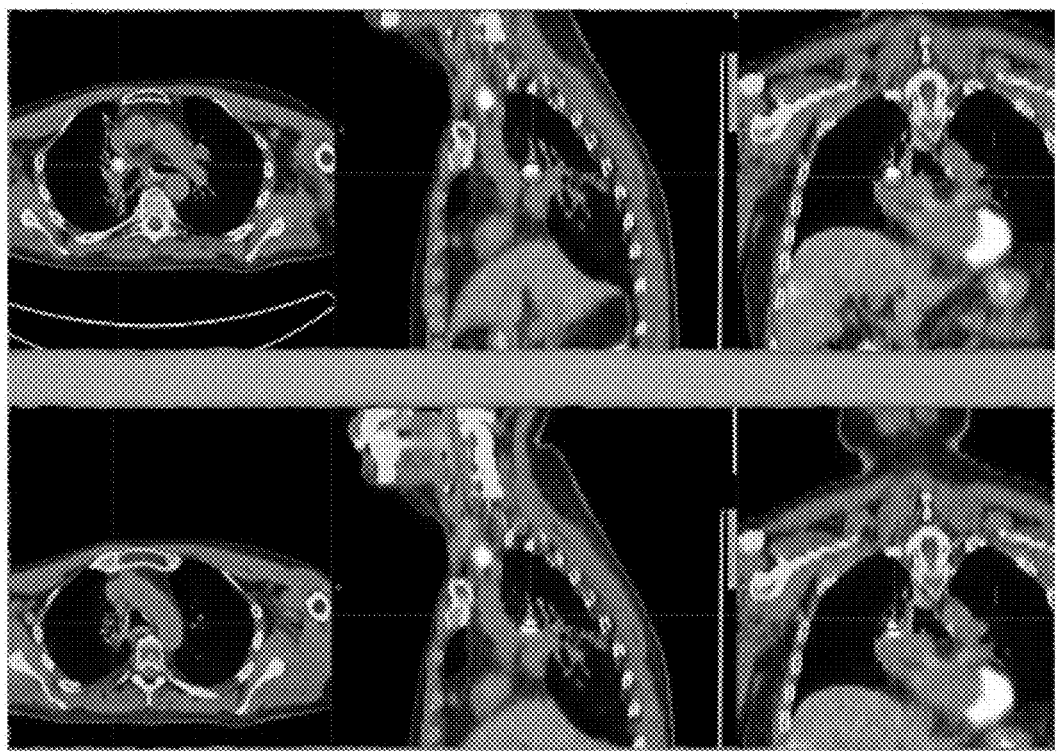
FIG. 7. The final images demonstrate response to treatment of the patient of FIGS. 5 and 6 (the patient of Example 2).
Figure 8:
FIGS. 8, 9, 10 and 11 represent the disease at the time of presentation for the patient of Example 3.
Figure 9:
Figure 10:
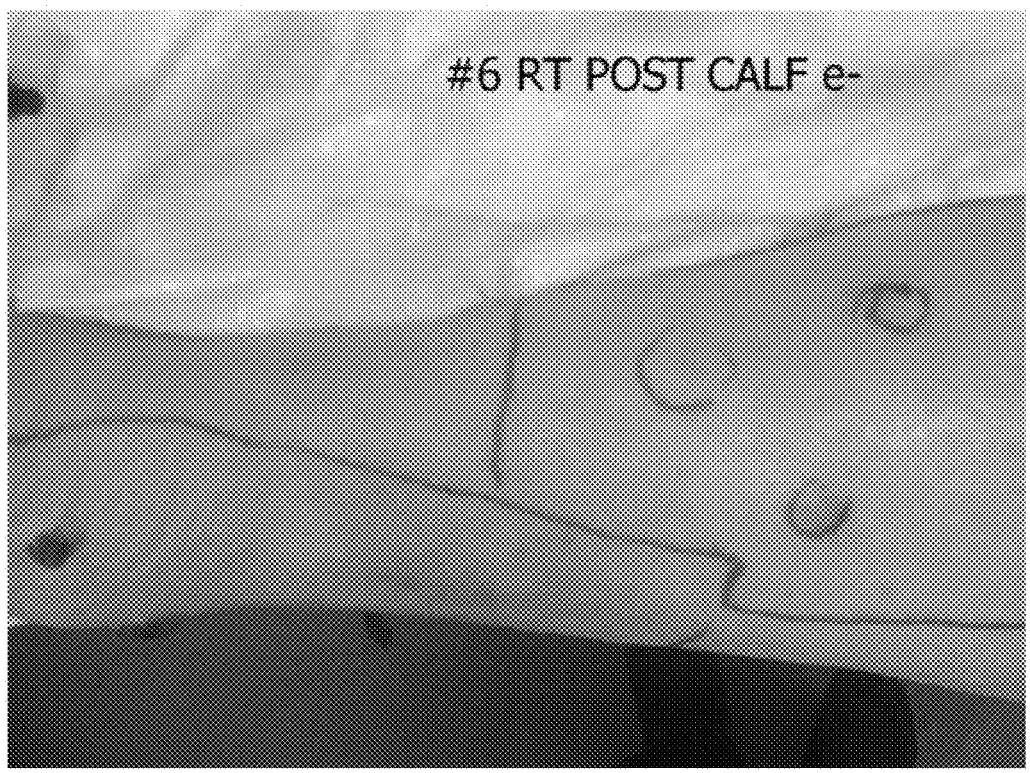
Figure 11:

Endoscopy evidenced impending obstruction. Biopsies were consistent with metastatic malignant melanoma. Definitive radiation was administered to the chest over the span of about one month and was delivered at 135 cGy per fraction twice-daily utilizing conventional photon therapy. The total dose to the lung was 5670 cGy. The first PET/CT scan following the completion of radiation therapy demonstrated significant inflammatory changes consistent with treatment intervention (FIG. 6). The final images demonstrate the dramatic response to treatment (FIG. 7).

The region in the superior chest demonstrating activity did not undergo radiation. This approach was requested by the medical oncology staff at the Moffitt Cancer Center that this area not be treated so that any form of systemic therapy delivered later would provide a marker to judge response. Because of the dramatic results achieved following radiation, the patient refused any form of systemic (targeted/ immunotherapeutic) intervention, and the remaining area was subsequently addressed successfully with radiation.

Example Three

An 83 year old noticed an ulcerative lesion involving the skin of her right ankle. She developed cellulitis and was placed on several antibiotics. "Red spots" involving the right ankle increased in size with biopsy showing melanoma with a thickness of 1.8 mm, Level IV.

The patient was initially evaluated at the University of Florida, and referred to the Moffitt Cancer Center. Yervoy could not be used due to the patient's renal status. Although Keytruda was considered, its systemic side effect profile negated that treatment option from her consideration; thus, the patient received no targeted/immunotherapeutic intervention. FIGS. 8, 9, 10 and 11 represent the disease at the time of presentation.

A PET/CT demonstrated soft tissue thickening with subcutaneous edema overlying the posterior lateral right ankle with numerous FDG avid soft tissue nodules in the right lower extremity to the level of the proximal femoral artery, demonstrating SUVs of 7.3. This study, performed at the University of Florida, was with the following report: "A bulky soft tissue FDG avid mass centered in the proximal anterior compartment of the right thigh adjacent to the femoral vessels measuring 4.0×4.7 cm in greatest axial dimension and demonstrating an SUV of 7.3, encases the right femoral artery." She was diagnosed with Stage IIIC malignant melanoma.

The surgical oncology department at the Moffitt Cancer Center recommended a radical lymphadenectomy of the entire right lower extremity, extending into the groin. The patient refused surgical intervention. The patient was seen and physical examination revealed elephantiasis of the right lower extremity, with 3+ pitting edema from the toes proximally. Multiple cutaneous nodules could be visibly and palpably appreciated to the level of the groin. Individual adenopathy to greater than 4.0 cm in size was found along the medial aspect of the right thigh, corresponding to the PET/CT scan findings.

The patient received twice daily radiation to multiple areas of the right lower extremity and pelvis, with total doses ranging from 3645 cGy, 5130 cGy, and 5265 cGy, administered at rates of 115-135 cGy per fraction.

Figure 12:
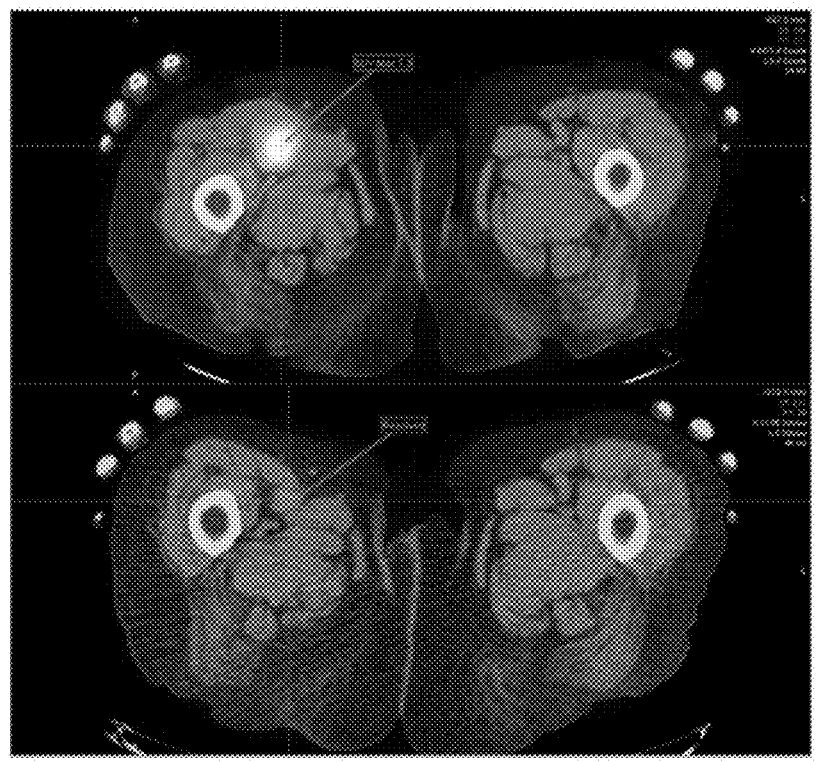
FIG. 12 compares the pre- and post-treatment appearance of the right medial thigh 4.7×4.0 cm lesion for the patient of Example 3.
Figure 13:
FIGS. 13 and 14 demonstrate complete visible resolution of the prior melanoma of the leg for the patient of Example 3.
Figure 14:

A subsequent PET/CT revealed complete resolution with normal PET imaging. Physical examination revealed no visible evidence of the prior malignancy. The right leg returned to normal size, and was equal with the left leg. FIG. 12 compares the pre- and post-treatment appearance of the right medial thigh 4.7×4.0 cm lesion. The remaining FIGS. 13 and 14 demonstrate complete visible resolution of the prior melanoma of the leg.

Example Four

A 61-year-old former pharmaceutical representative was found to have a lesion involving the skin of the lower back at the level of L4. Biopsy revealed malignant melanoma in situ, with complete surgical excision. Two weeks prior to our evaluation, a "golf ball" size right axillary mass was found. Mammography and ultrasound demonstrated an abnormally enlarged lymph node measuring 2.7 cm, confirmed on PET/CT, whose activity was markedly elevated with an SUV of 15.2 units. Biopsy-only proved metastatic malignant melanoma.

Figure 15:
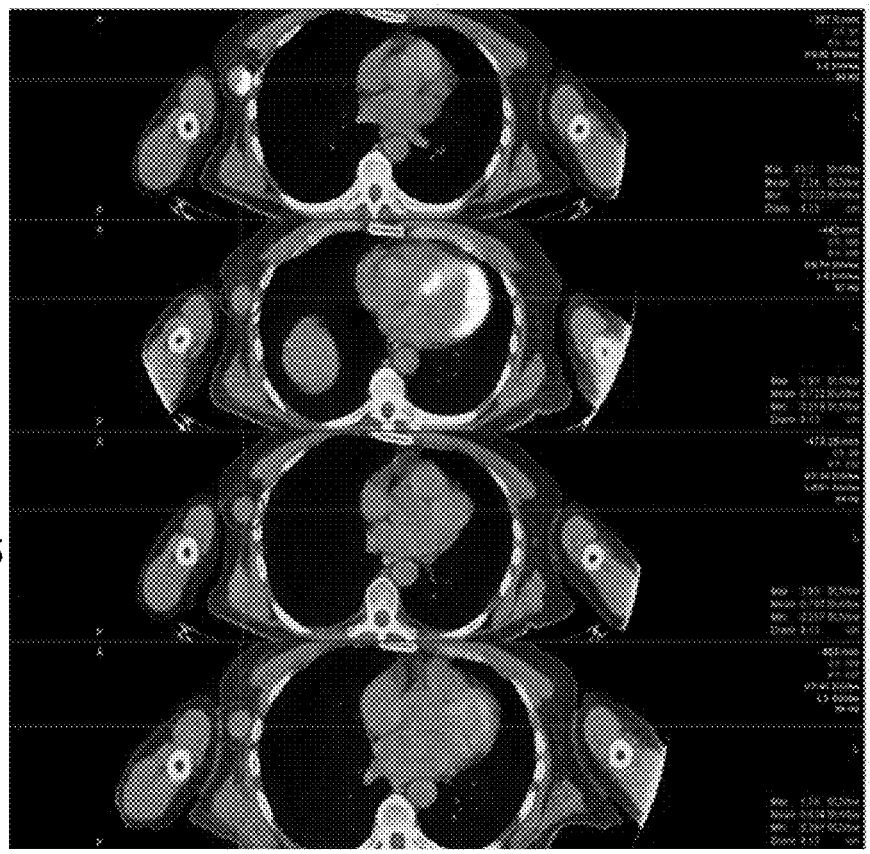

Physical examination revealed a firm 2.7 cm mass tethered to the underlying axillary structures. Definitive radiation treatment was administered over the span of about two months. The patient received a total of 6480 cGy, delivered at 135 cGy per fraction twice-daily. He is now 22 months from treatment, with both physical examination and radiographic studies demonstrating no evidence of local/regional recurrence and no metastatic disease. The patient did not receive immunotherapeutic intervention. FIGS. 15 and 16 represent serial PET/CT scans, including the original as well as follow-up scans.

Example Five

The first resection for this gentleman was for a melanoma lesion involving the skin of the right shoulder. A second lesion was resected a number of years later and confirmed to be spindle cell melanoma. Biopsy of a third left chest lesion showed melanoma, widely excised with negative margins.

The patient was followed at the Moffitt Cancer Center, as well as Roswell Park in Buffalo. Subsequently, a left posterior shoulder lesion proved his fourth primary melanoma and a CT scan revealed a tumor in the right chest invading the right bronchus intermedius. A PET/CT found disease in the right lower lobe extending into, and inseparable from, the right hilum. The overall size of the mass measured 6.5×4.7×4.7 cm, and demonstrated a metabolic activity of 12 units. In addition, left upper lobe parenchymal metastatic disease was found measuring 1.7×1.7×1.0 cm. Bronchoscopy revealed spindle cell melanoma cytology. When evaluated at the Moffitt Cancer Center, 100% obstruction of the right bronchus intermedius was found, with the airway debulked. Pathology confirmed malignant melanoma.

Although systemic intervention was recommended, the potential side effects caused the patient to decline this modality and he elected to proceed with radiation. He therefore received 6480 cGy and 5940 cGy to the right and left lung masses, respectively, at 135 cGy per fraction, delivered twice-daily over the span of about one month.

Figure 17:
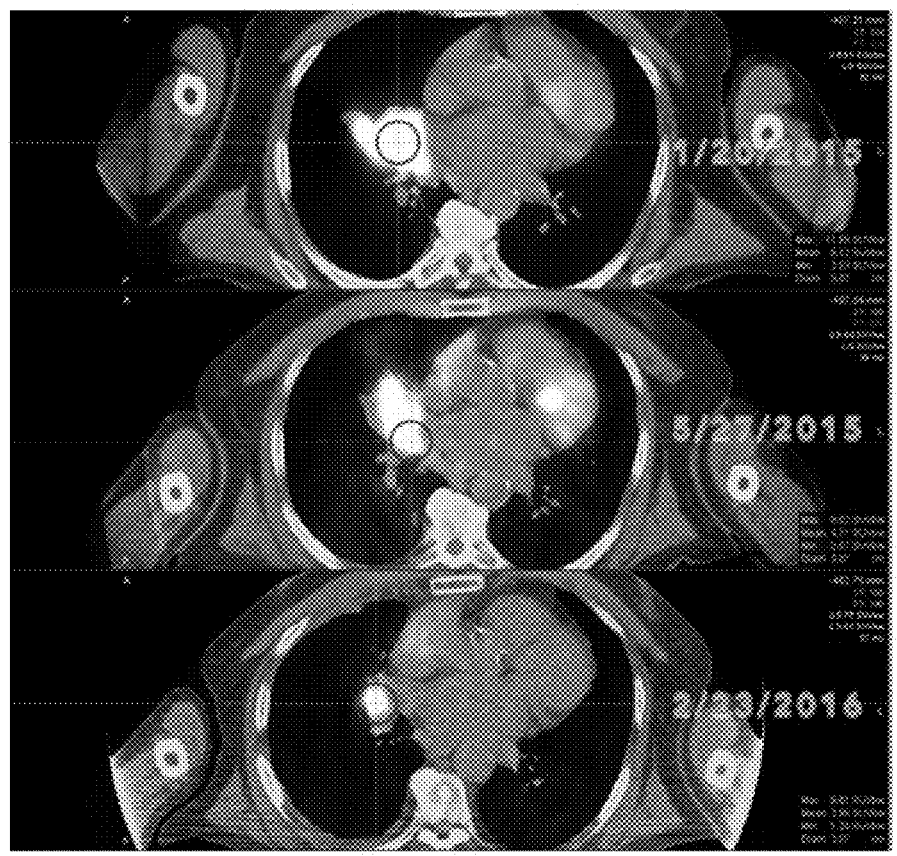
FIG. 17 compares serial PET/CT scans demonstrating continued regression of bulky pulmonary parenchymal disease, with volume comparisons, for the patient of Example 5.

Treatment with radiation led to improved breathing, with O2s above 98%. The patient returned to Buffalo for the summer. Repeat CTs at Roswell Park demonstrated continued linear regression of disease, with no further treatment intervention due to the patient's continued response to radiation. FIG. 17 compares serial PET/CT scans demonstrating continued regression of bulky pulmonary parenchymal disease, with volume comparisons.

Example Six

An 83-year-old gentleman was originally diagnosed with malignant melanoma in 1987, at which time he underwent a wide local excision for a lesion involving his left shoulder. Over two decades later, he presented with further but unrelated disease behind both the left ear and a separate left scalp nodule. Biopsy of the left mastoid area revealed malignant melanoma with a Breslow thickness of 2.0 millimeters and a Clark's level IV. Radical surgery with full thickness skin graft as well as wide removal of the left scalp nodule was performed. Pathology mandated further resection. A recurrence again required resection. Another recurrence was tested and revealed BRAF V600E. After 9 surgeries, he was begun on vemurafenib (Zelboraf), a targeted therapy, but experienced significant side effects. Reduction in dose did not resolve side effects, as the cancer's growth accelerated. Treatment was discontinued and the patient was told there were no further treatment options available.

Subsequently, he presented to me for evaluation and received radiation therapy over a period of about one month for a total dose of 5940 cGy, delivered at 135 cGy/fraction. No systemic intervention was administered.

Figure 18:
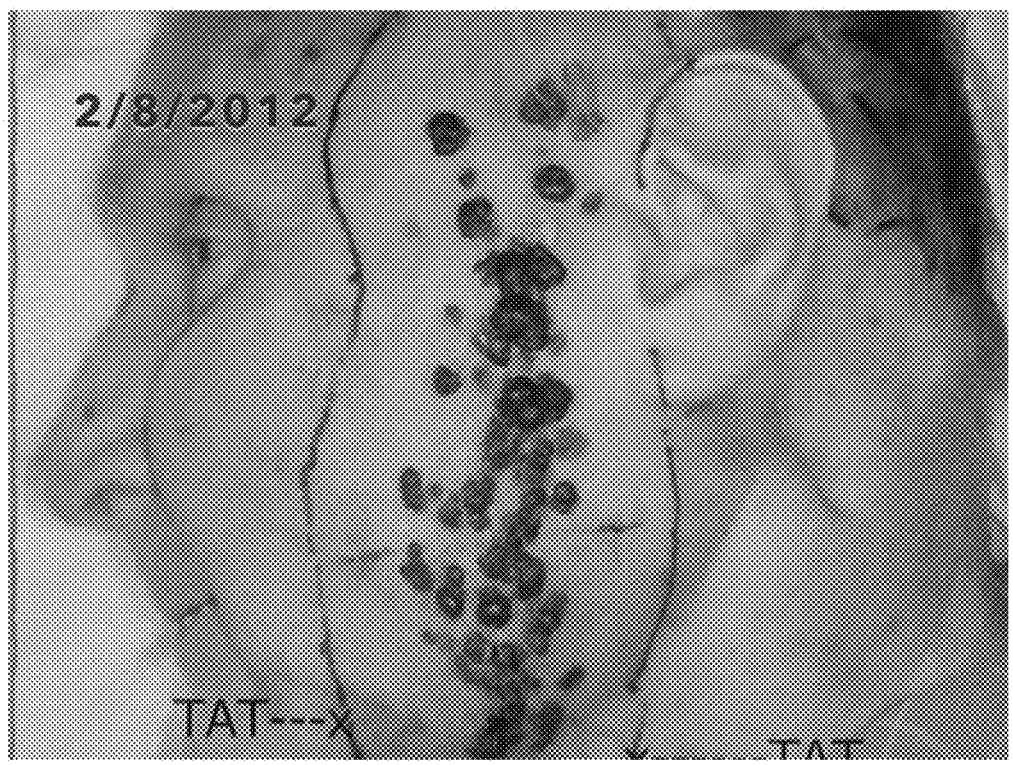
Figure 19:
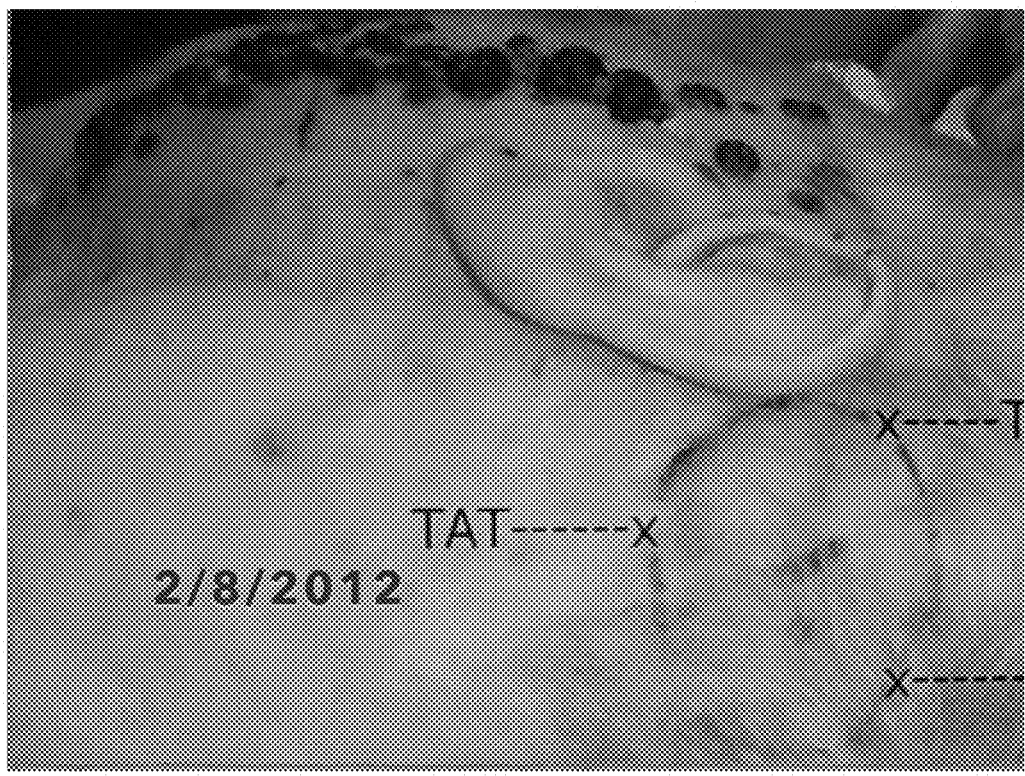
Figure 20:
Figure 21:
Figure 22:
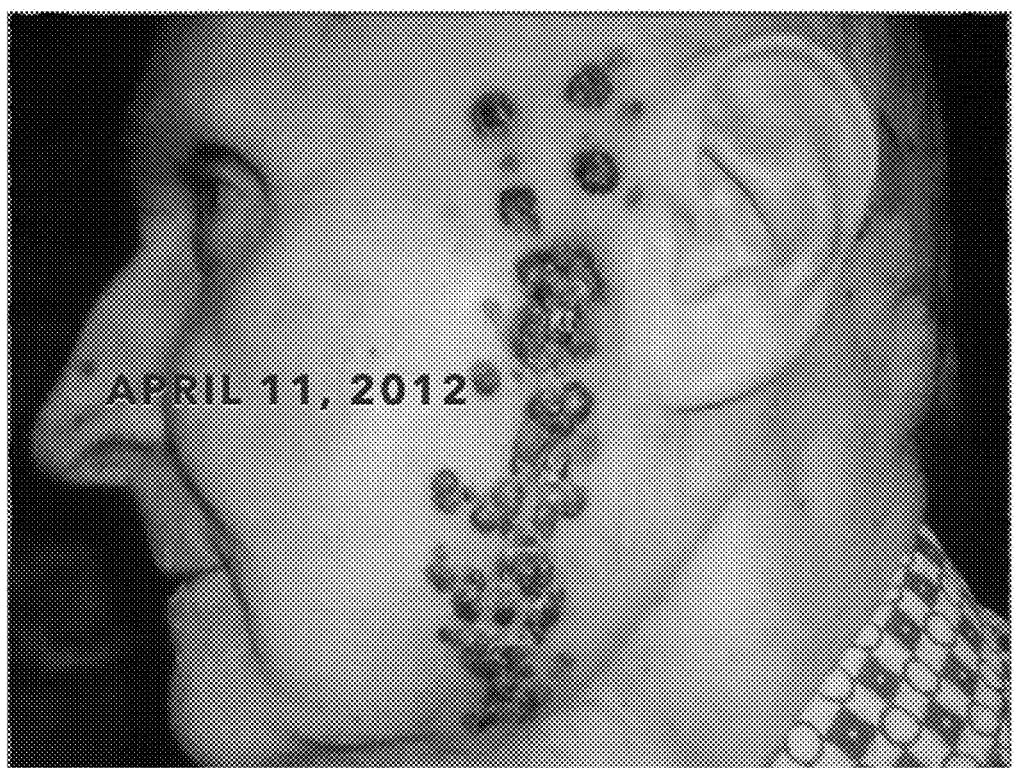
Figure 23:
Figure 24:
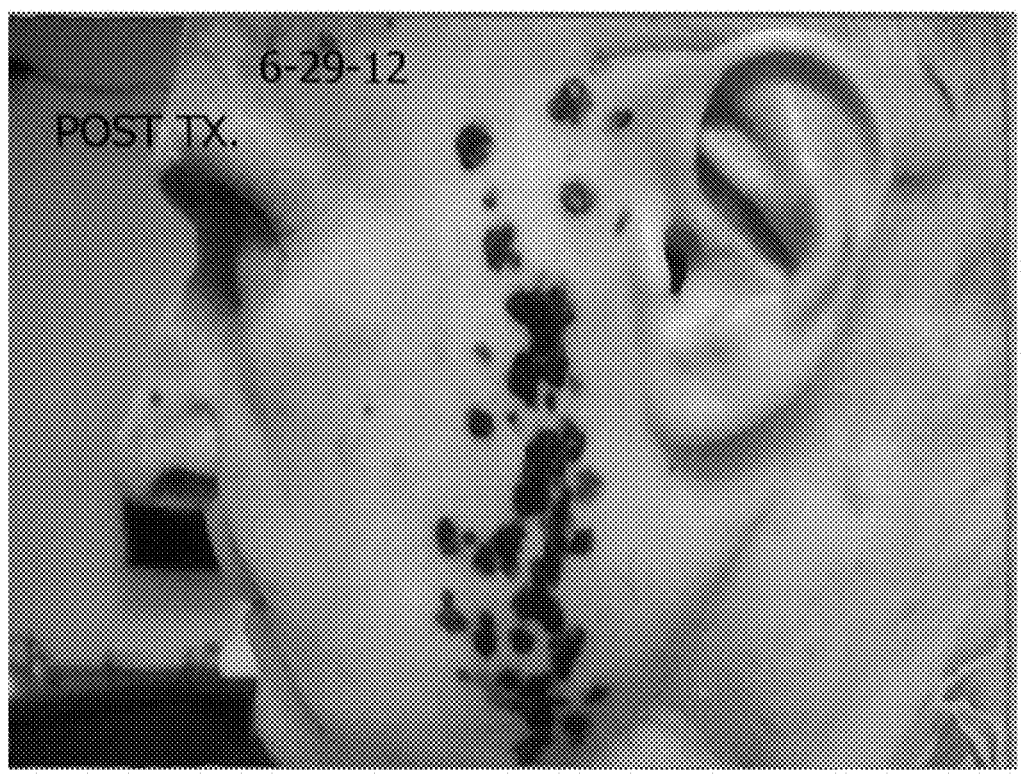
Figure 25:
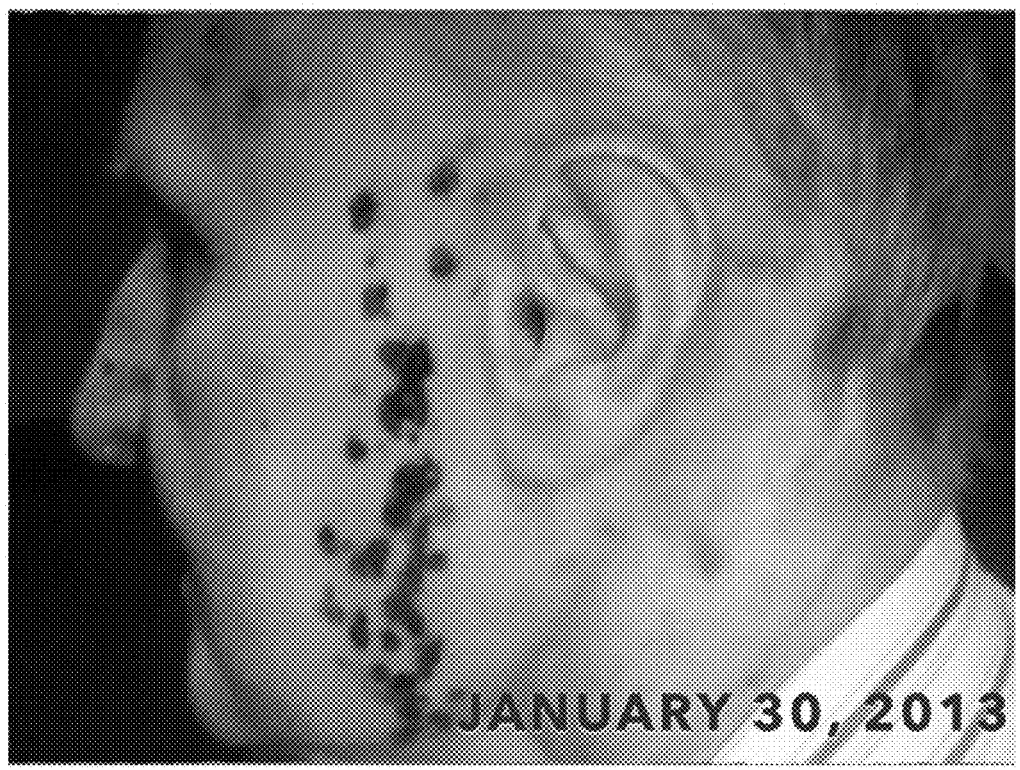
Figure 26:
Figure 27:
Figure 28:
Figure 29:
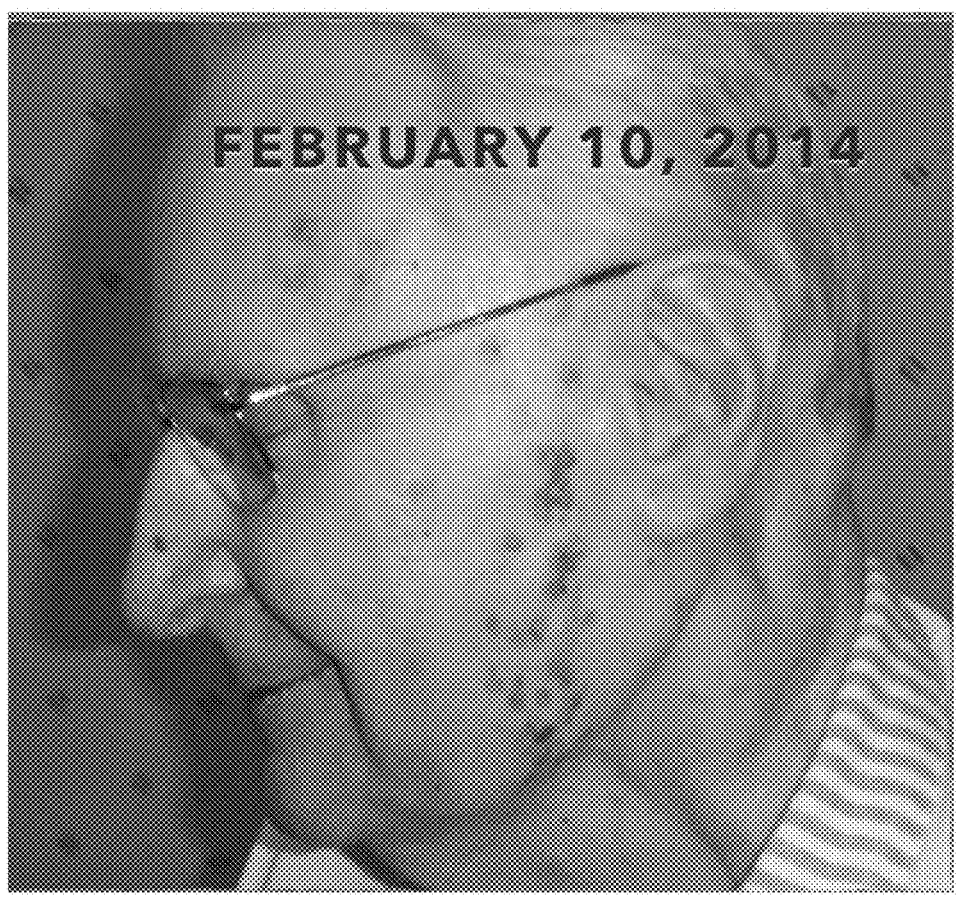
Figure 30:
Figure 31:
Figure 32:
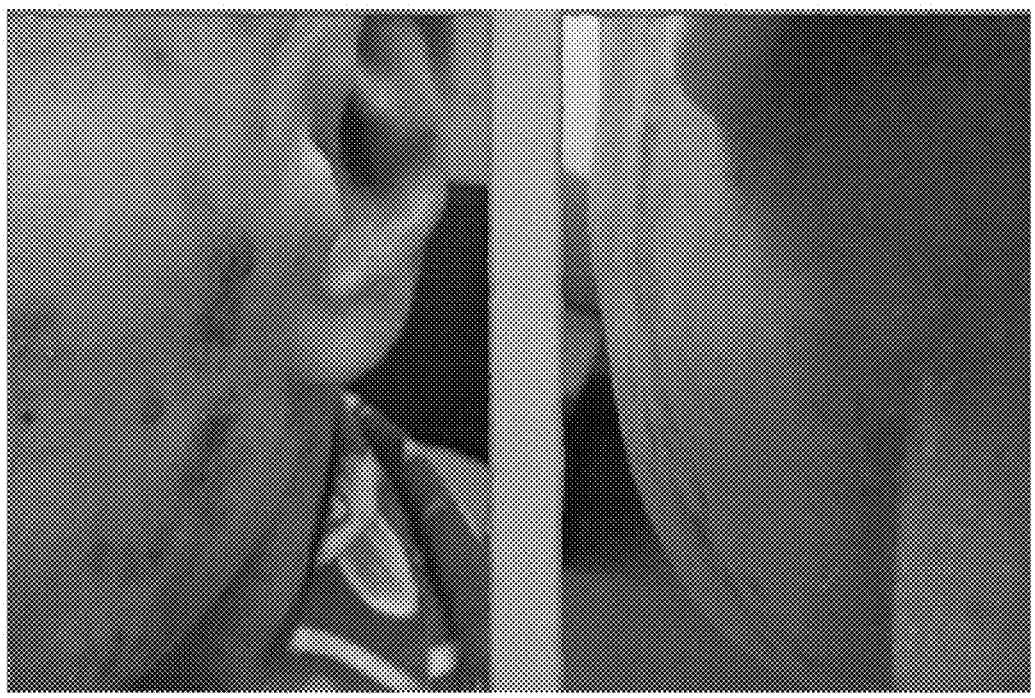
Figure 33:
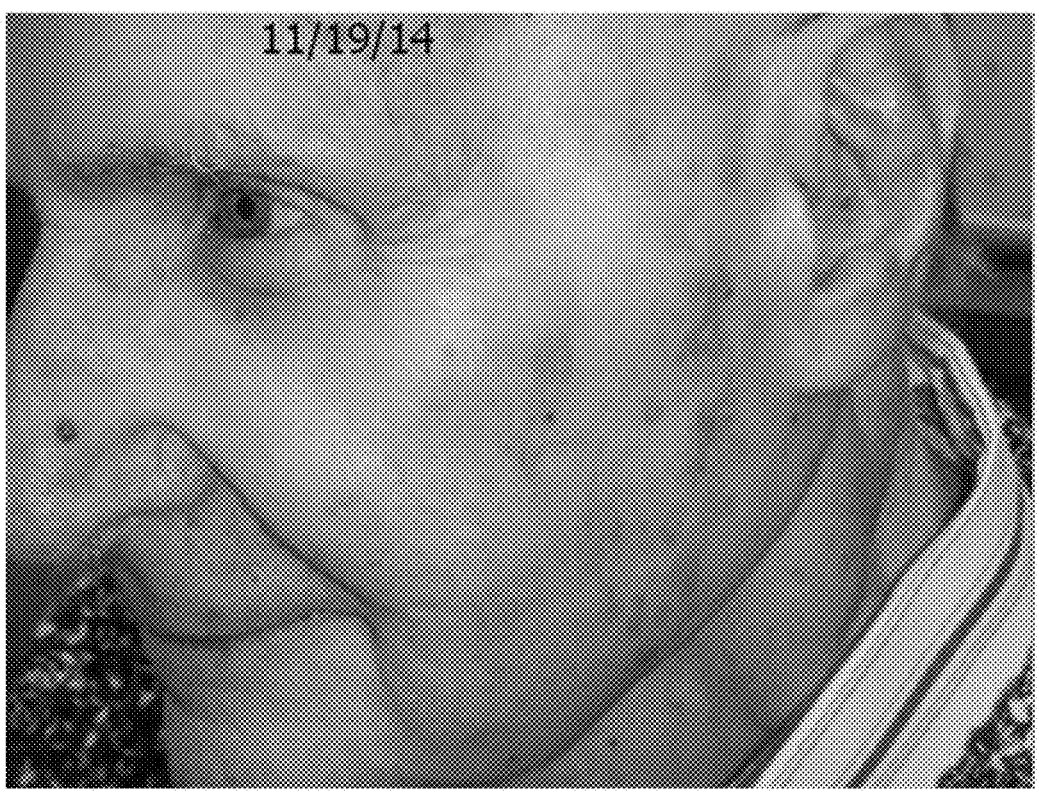
Figure 34:
Figure 35:
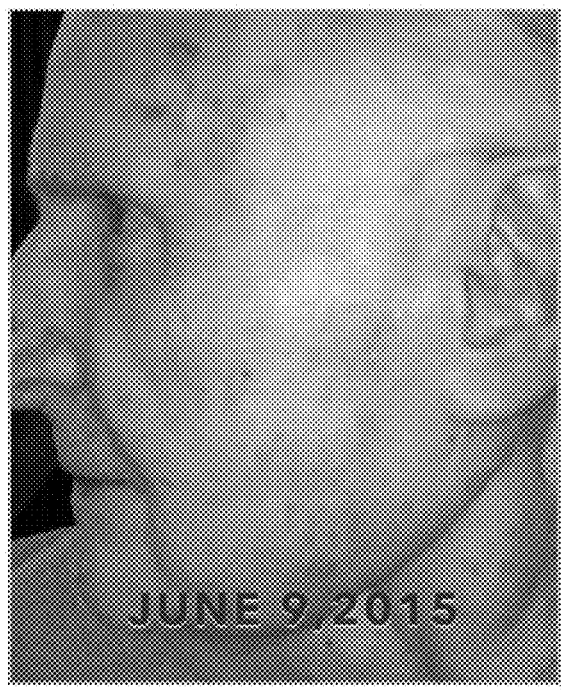
Figure 36:
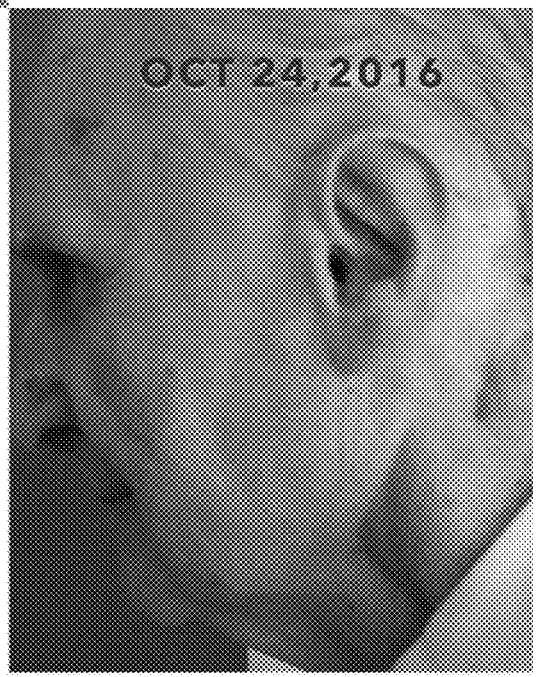

FIGS. 18 and 19 represent the appearance at the time of initial evaluation. FIG. 20 represents the appearance during the course of treatment, with FIG. 21 representing the appearance on the final treatment day. FIG. 22 represents the appearance at the first follow-up visit six weeks following the completion of treatment. The patient was followed over time and FIGS. 23-37 demonstrate the results. FIG. 37 is a comparison of the first post treatment documentation with that of the last follow-up visit. Close follow up has included physical examination (as documented in the accompanying photographs and serial PET/CT scans). The patient is without physical or radiographic evidence of recurrence or evidence of metastatic disease. In addition, there were no post treatment side effects from radiation. Repeat physical examinations reveal excellent maintenance of the skin without scar tissue formation. There has been no deficit in the patient's taste, smell, or hearing.

Example Seven

A respected pediatrician underwent removal of a left shoulder skin melanoma in. A left axillary 4 cm nodal conglomerate was found several years after resection, demonstrating extracapsular extension, with incomplete resection due to adherence to the chest wall.

An axillary dissection at the Moffitt Cancer Center revealed a positive 1.2 cm node without extra-capsular extension; BRAF wild type was found. The patient received post-operative radiation to the area of prior surgical resection for a period of about one month.

Figure 38:
FIGS. 38-46 relate to the effects of treatment for the patient of Example 7.

A follow-up PET/CT revealed a RUL 9-10 mm pulmonary nodule, with an SUV of 3.5, felt by Moffitt Cancer Center to be metastatic malignant melanoma (FIG. 38).

The patient was treated for about one month at the site of the lung lesion with twice-daily radiation, delivered at 135 cGy per fraction to 6210 cGy total dose.

Figure 39:
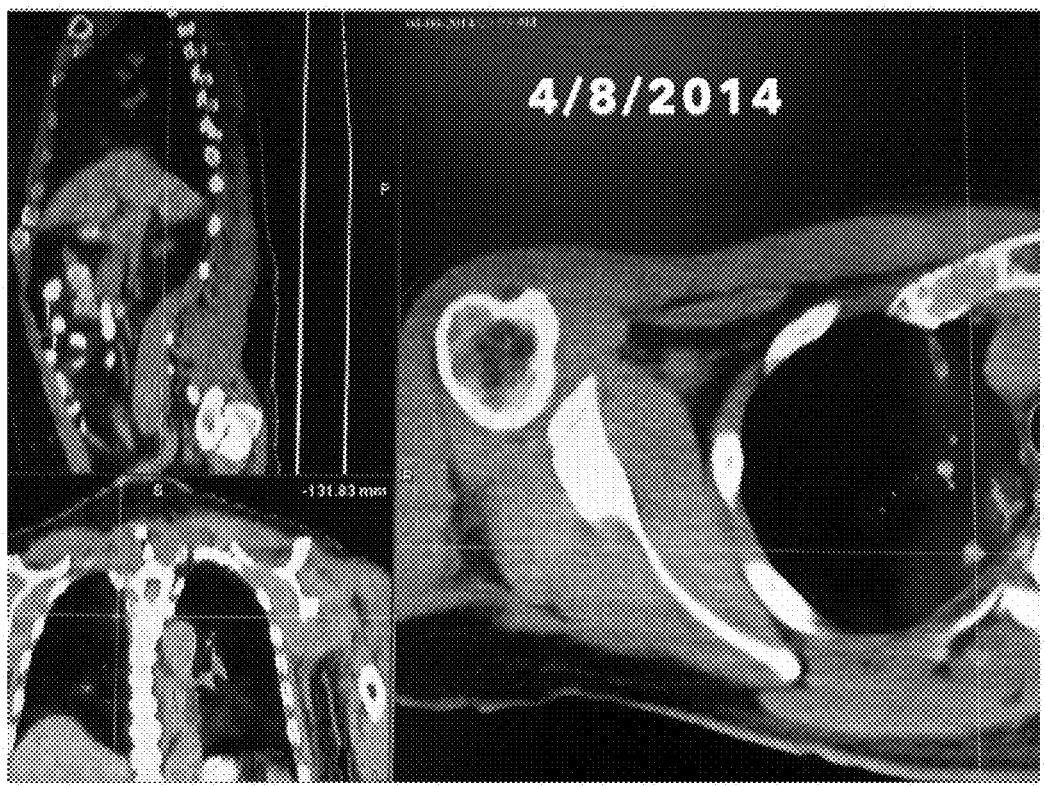
Figure 40:
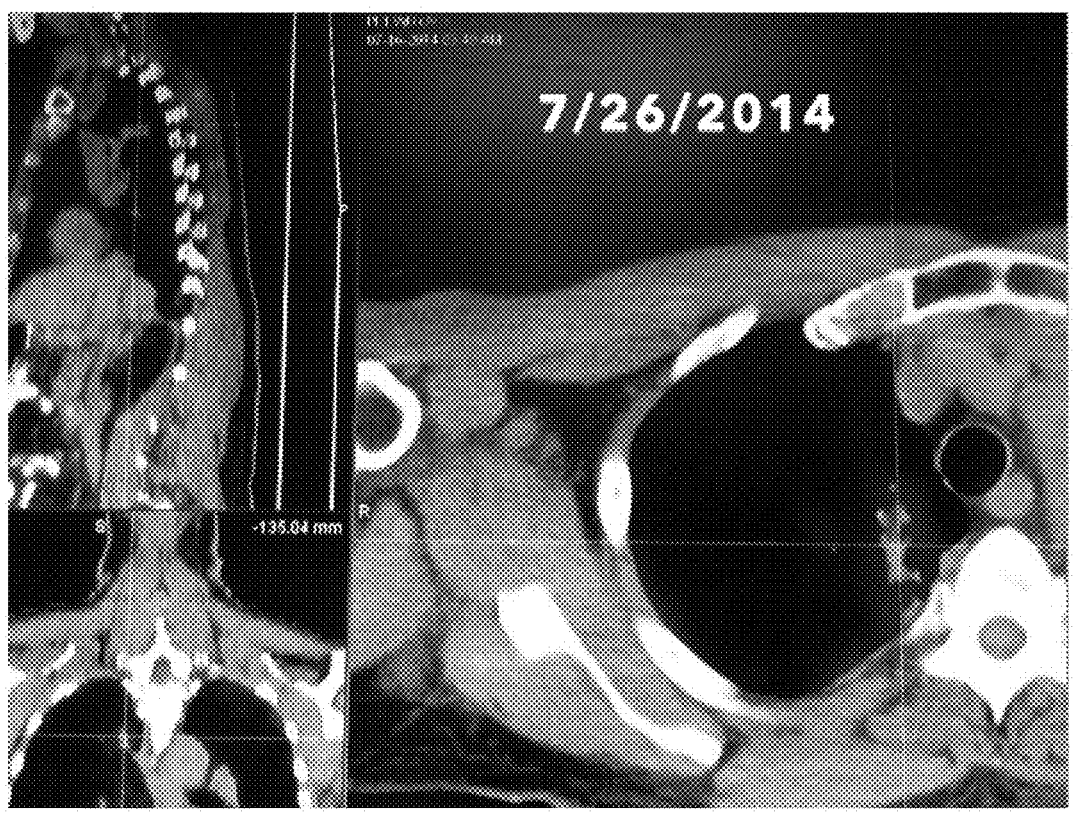
Figure 41:
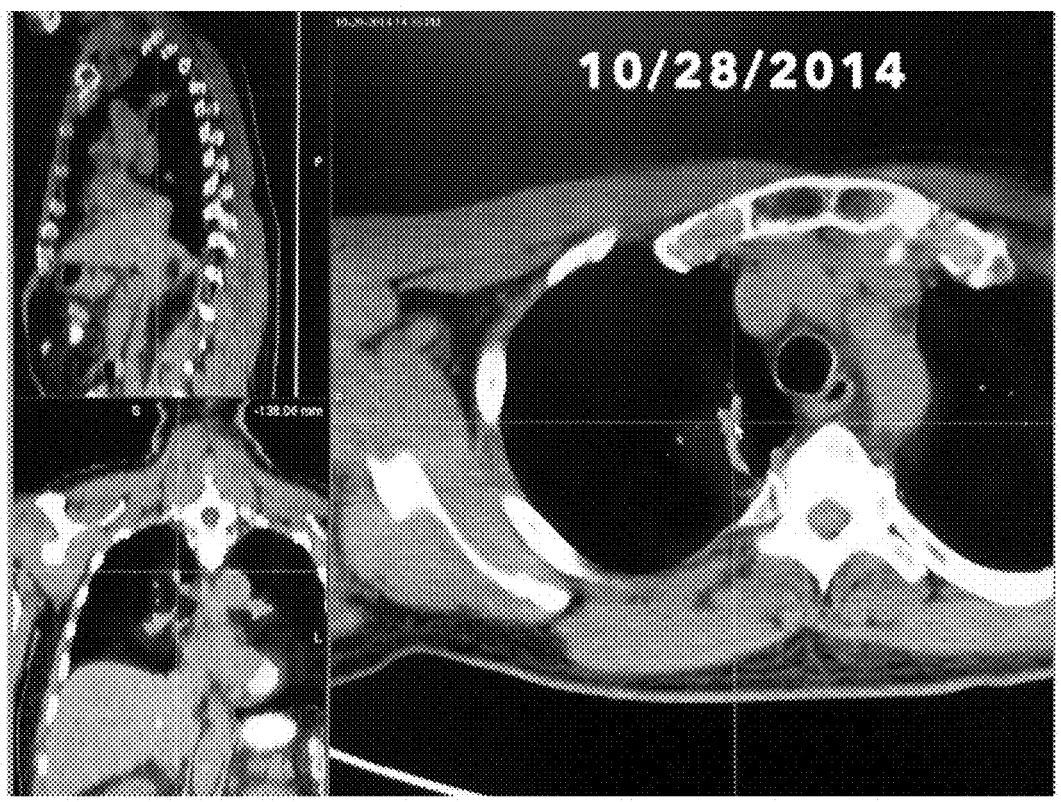
Figure 42:
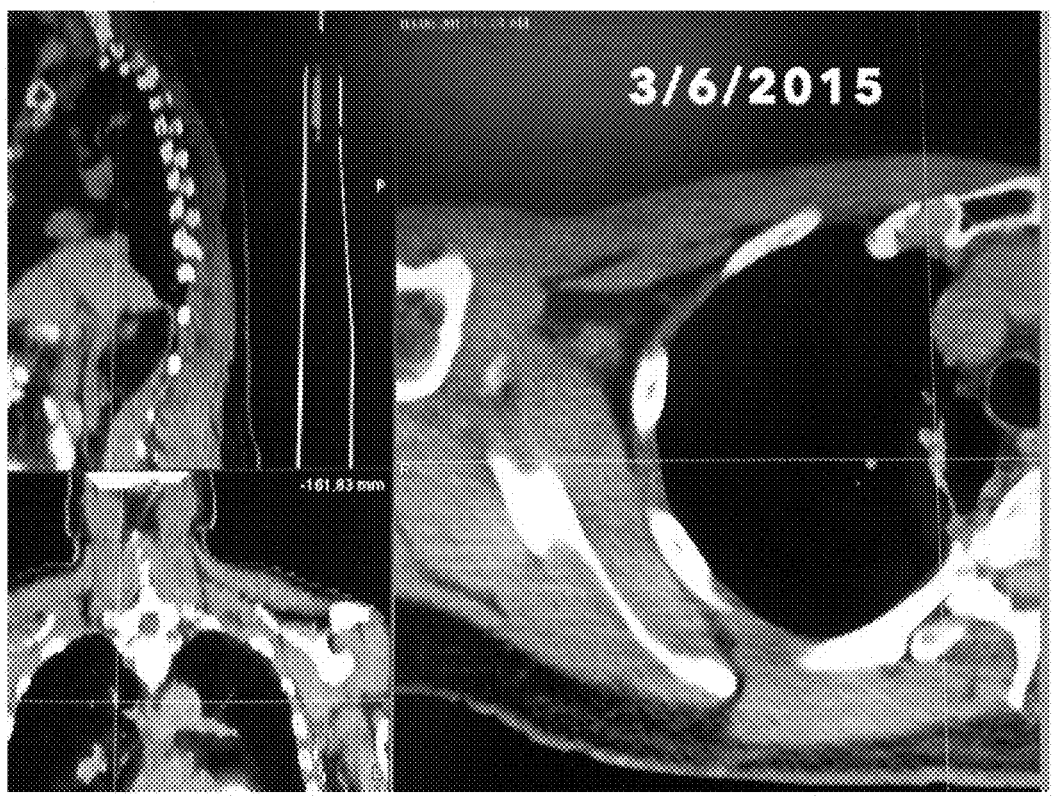
Figure 43:
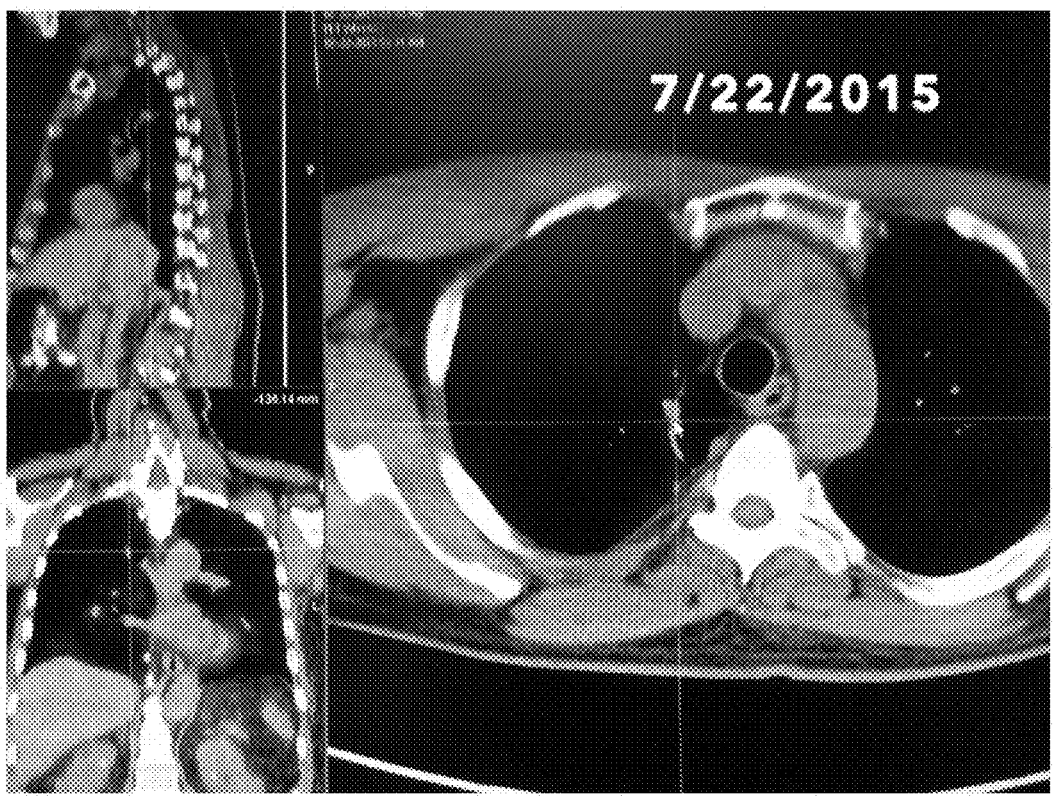
Figure 44:
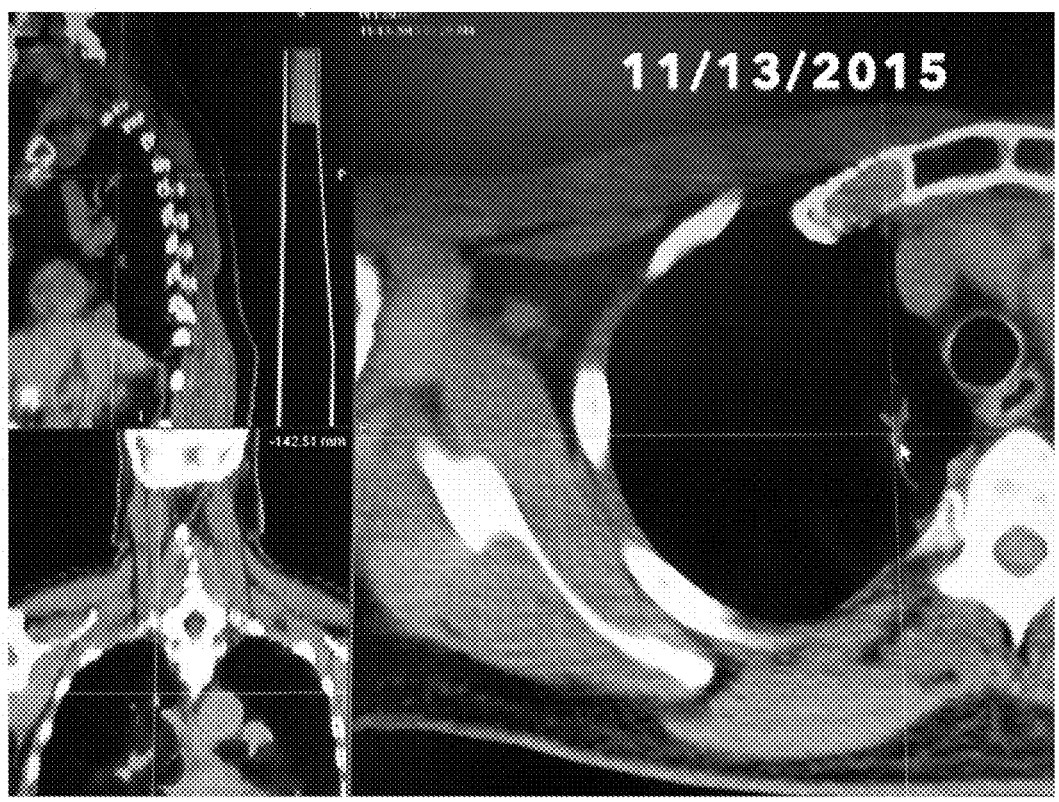
Figure 45:
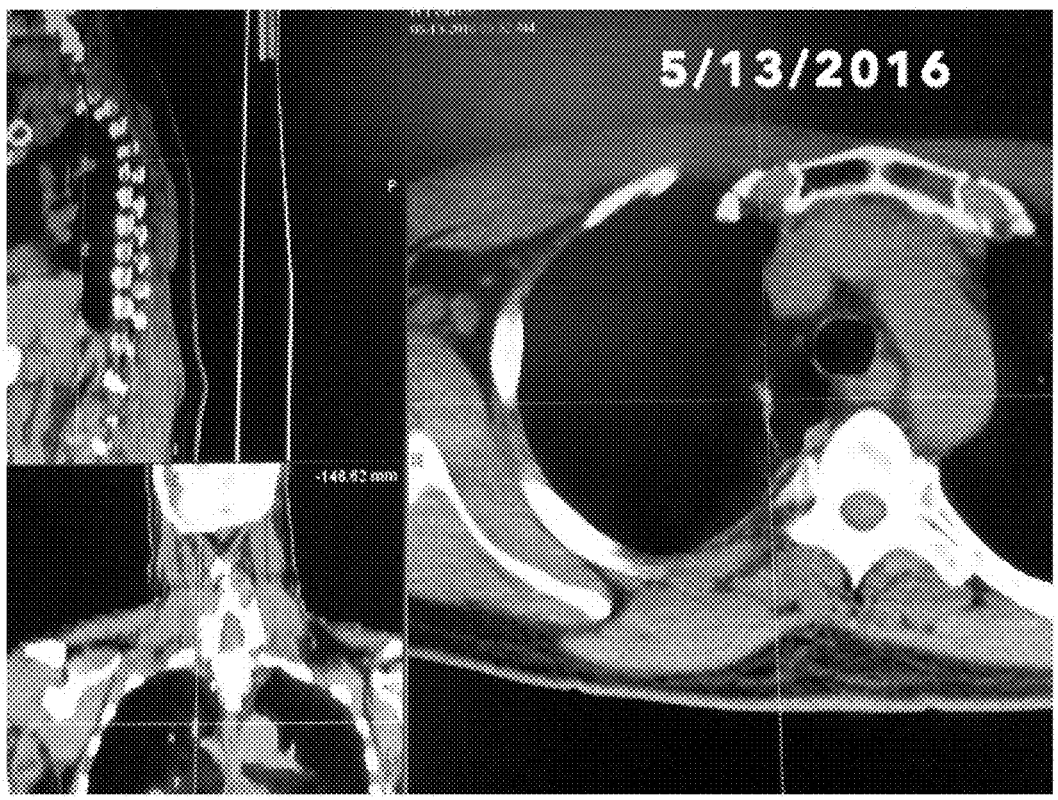
Figure 46:
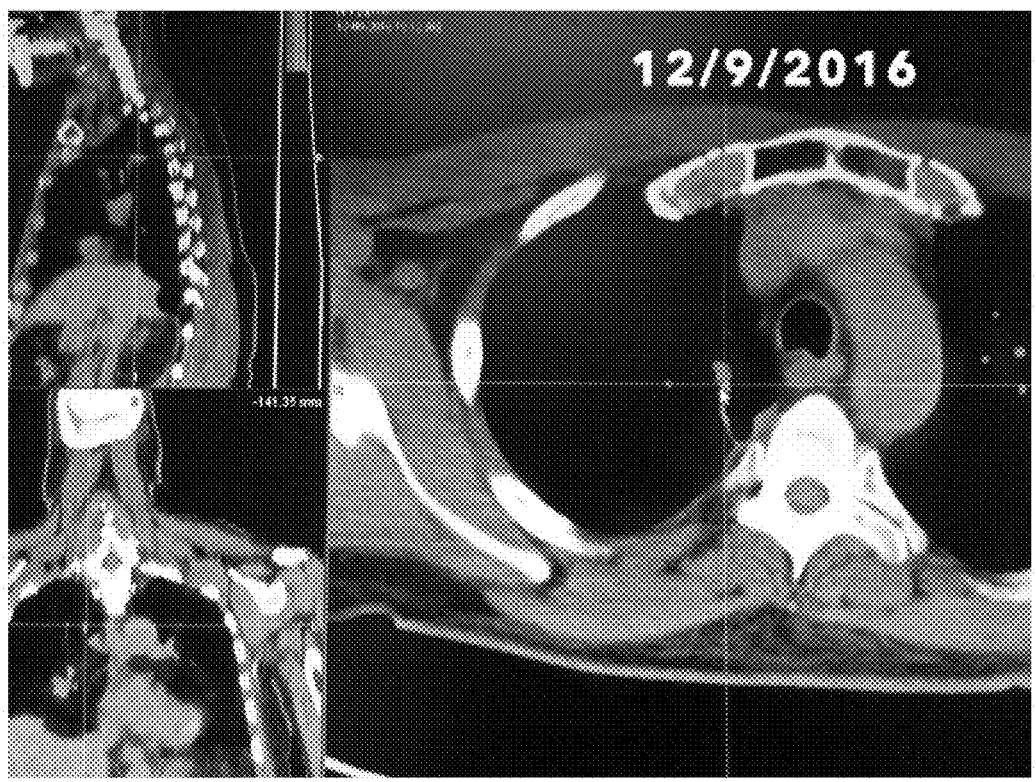

A PET/CT (FIG. 39) demonstrated a decrease in both size and metabolic activity; serial PET/CTs (FIGS. 40-46) were performed demonstrating fibrotic changes consistent with treatment, but no evidence of recurrence or metastatic disease.

Example Eight

A 60-year-old male was diagnosed with a malignant melanoma involving the left shoulder. Melanoma occurred in the right temporal region several years later, with subsequent removal. This was followed by a resection and lymph node dissection, performed at the Moffitt Cancer Center, with pathology from the resection specimen and nodes to be negative.

Figure 47:
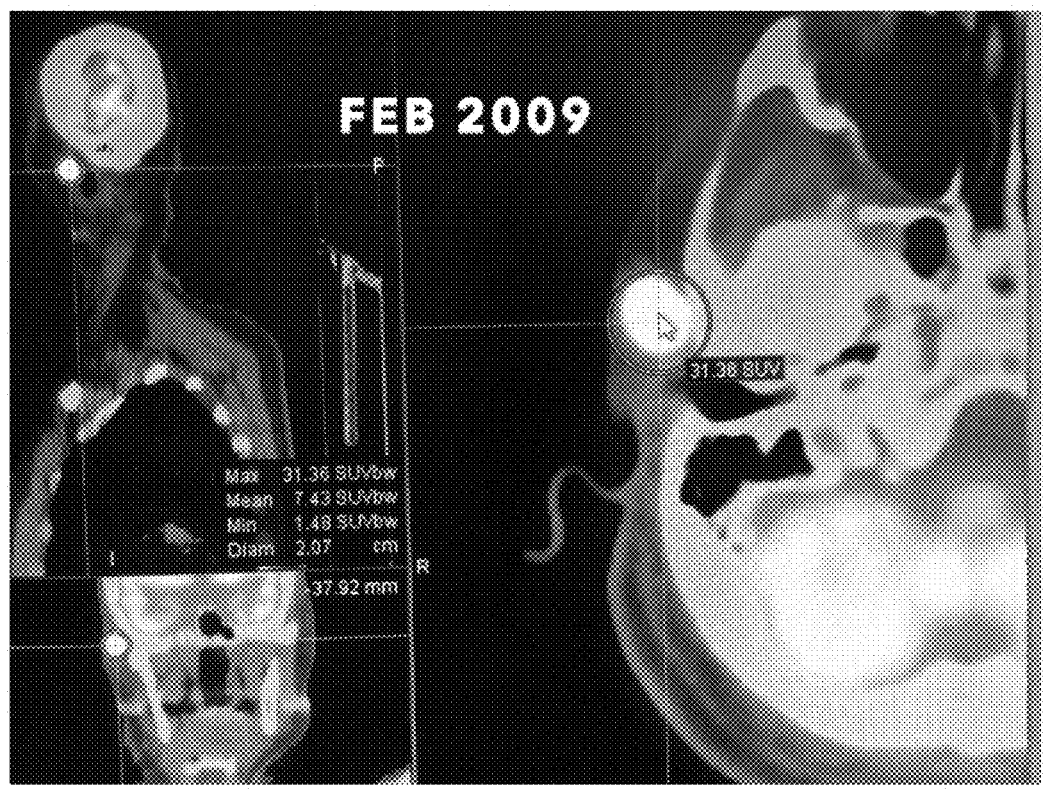
FIGS. 47-54 relate to the effects of treatment for the patient of Example 8.
Figure 48:
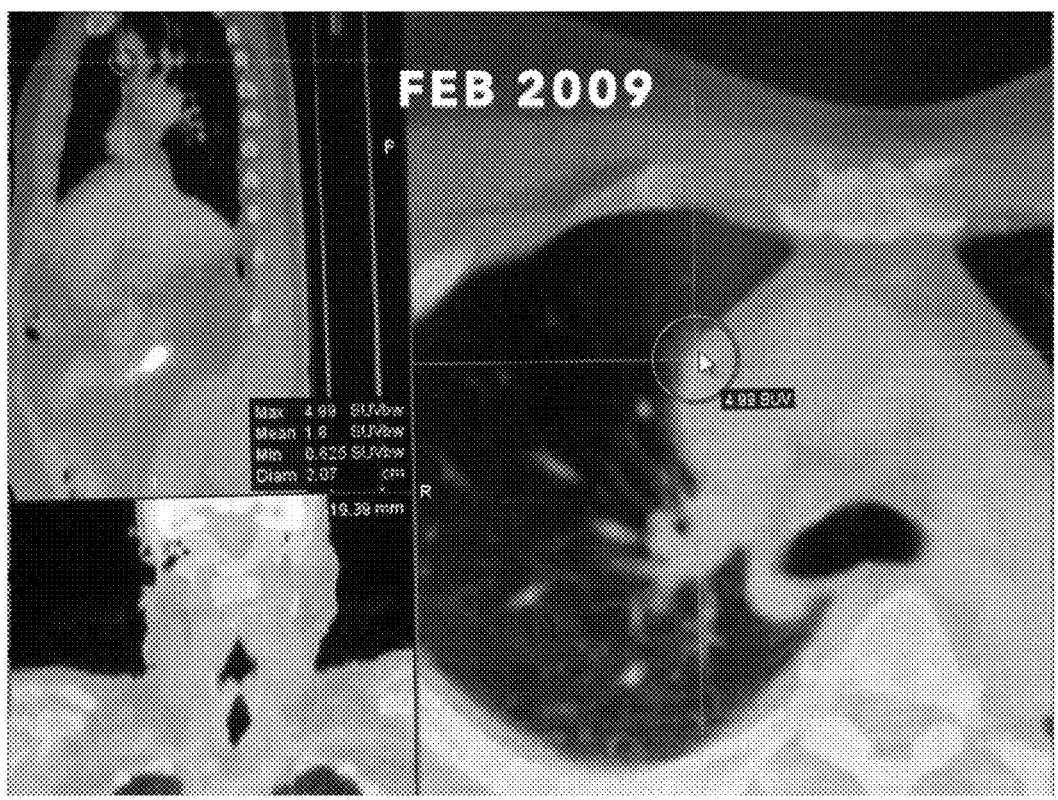
Figure 49:
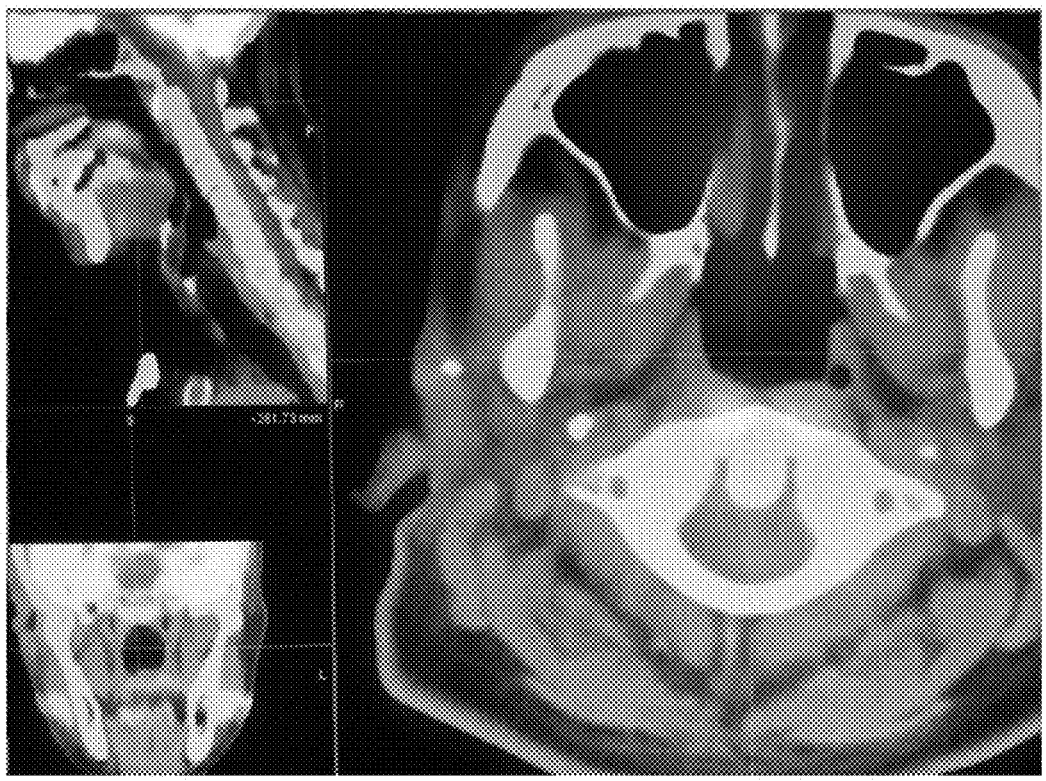
Figure 50:
Figure 51:
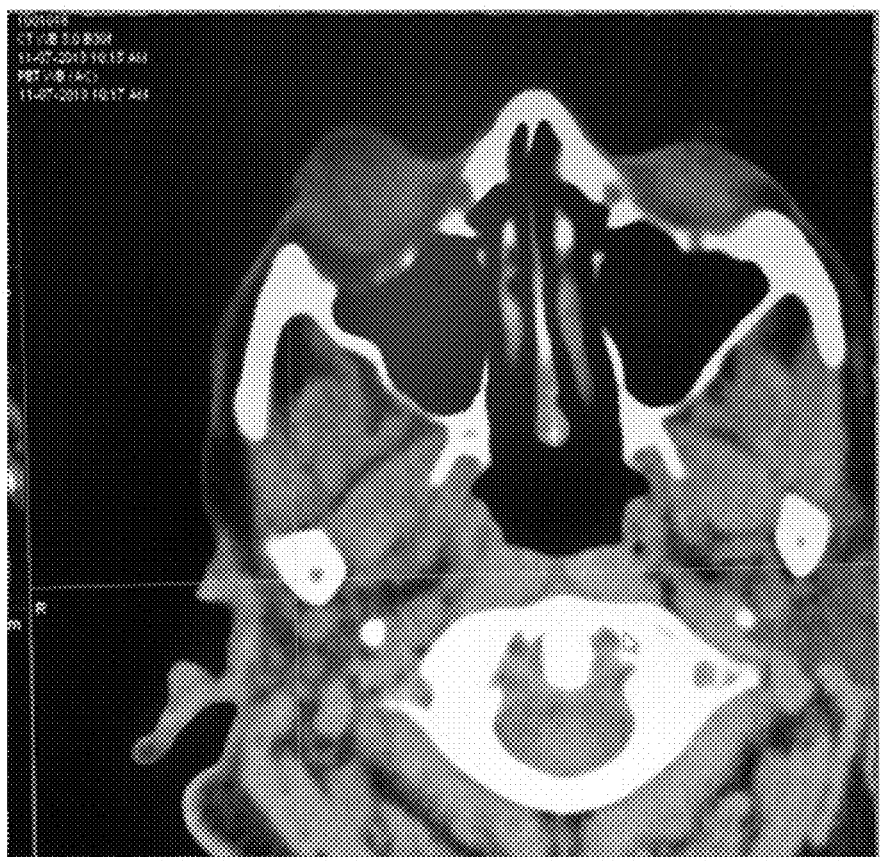
Figure 52:
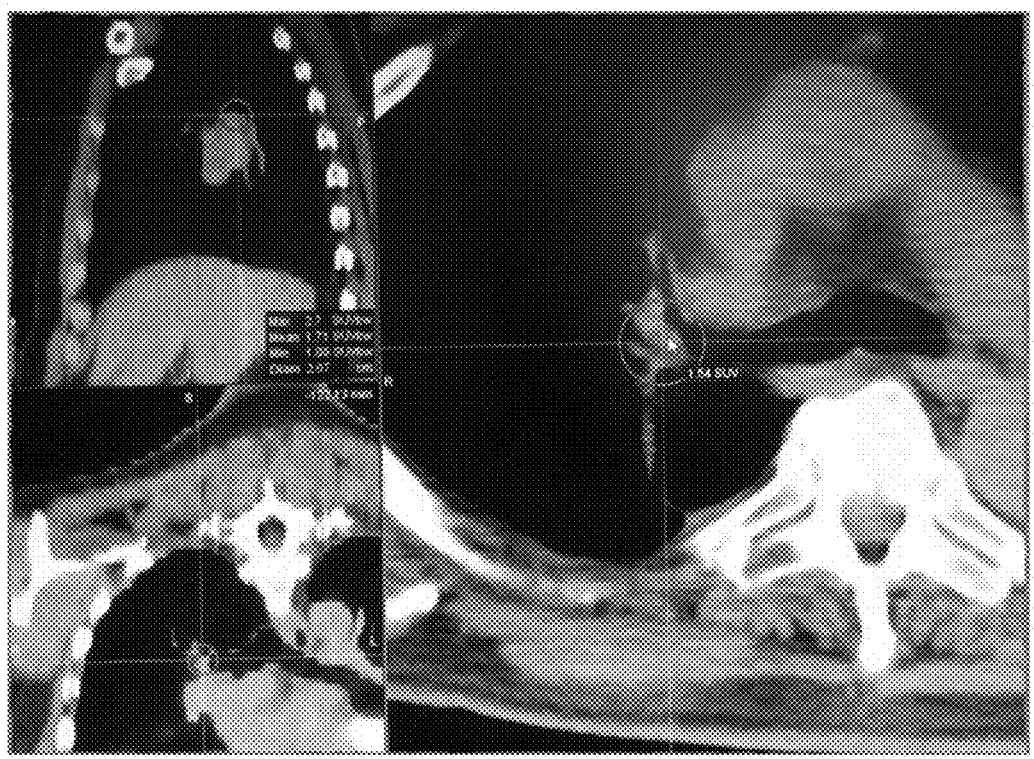
Figure 53:
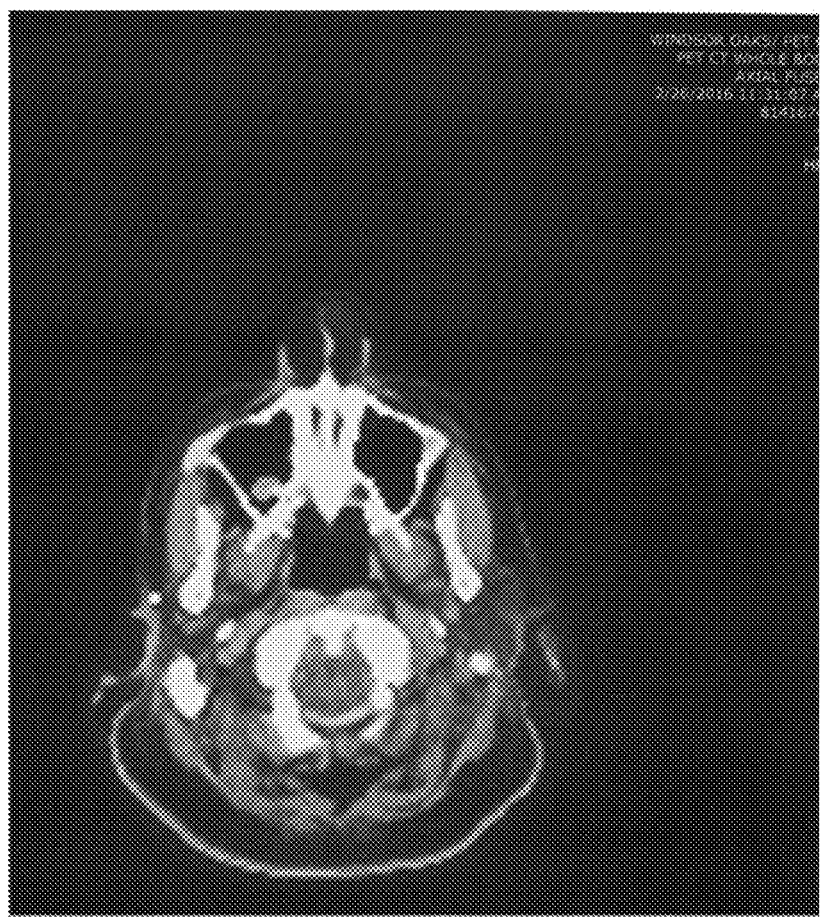
Figure 54:
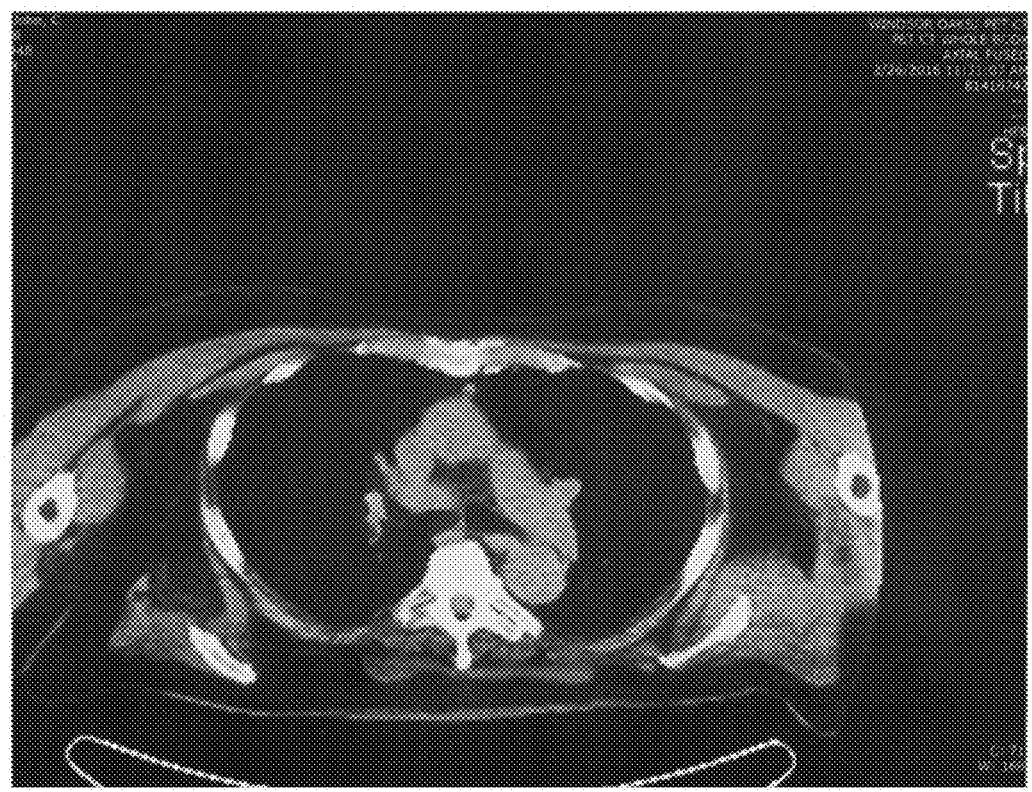

Subsequently, a PET/CT scan revealed a 2 cm right facial mass contained within the preauricular region; SUV was markedly elevated to 31.4 units (FIG. 47). At the same time, a hypermetabolic 5 mm right upper lobe nodule was seen in the chest, demonstrating an SUV of 5 (FIG. 48). The patient was scheduled to undergo thoracotomy and resection of the right lung lesion first, with evaluation of the right preauricular region to be forthcoming thereafter. Testing demonstrated a BRAF wild type melanoma.

The patient declined surgical intervention, and proceeded with definitive twice-daily radiation. Treatment was delivered over the period of about one month and was delivered using a combination of photon/electron therapy to the right face and proximal regional nodes; photon energy was delivered to the lesion within the lung. Treatment was administered at 135 cGy per fraction, administered twice-daily for a total dose of 6460 cGy to both areas of involvement. The patient is now 94 months since the initiation of treatment, without evidence of recurrence within either treatment volume. No diminishment in quality of life has been observed. (FIGS. 49-54 document control of both sites of disease.)

The patient did develop further disease outside of the areas of original treatment, when resection of a right neck mass revealed metastatic malignant melanoma. Four cycles of Yervoy were administered during the patient's radiation therapy. A total of 5400 cGy was delivered at 135 cGy per fraction, administered twice daily. The patient is now more than 24 months from the out of field recurrence, without physical evidence of local/regional or further metastatic disease. In addition, the last PET/CT scan was performed with "no clear evidence of metastatic disease. No definite significant abnormal FDG activity."

Data

Figure 55:
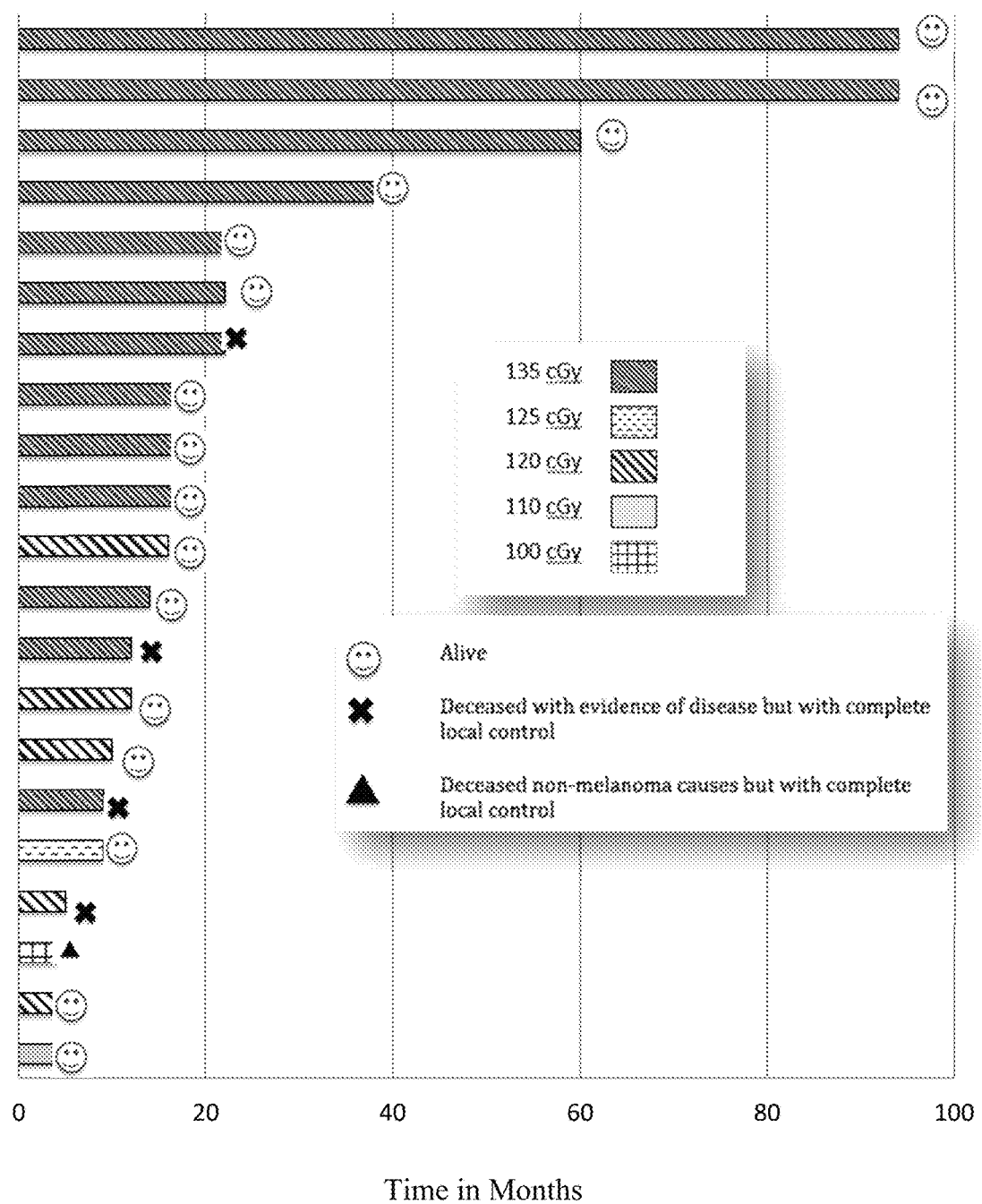
FIG. 55 shows a variance of dose per fraction regimens for patients treated with locally advanced disease, as well as macroscopic metastatic disease compared to survival over time.

FIG. 55 utilizes a variance of dose per fraction regimens for patients treated with locally advanced disease, as well as macroscopic metastatic disease compared to survival over time. It is evident that the optimal dose per fraction is still not clearly defined. The biological effect, however, is well documented with 100% complete/continued regression. One death has occurred from unrelated causes, with the remaining few deaths occurring from disease progression outside the area of local/regional control. FIG. 55 illustrates complete/continued regression of visible/radiographic disease within treatment volume. Dose per fraction (treated twice a day) is also provided.

Figure 56:
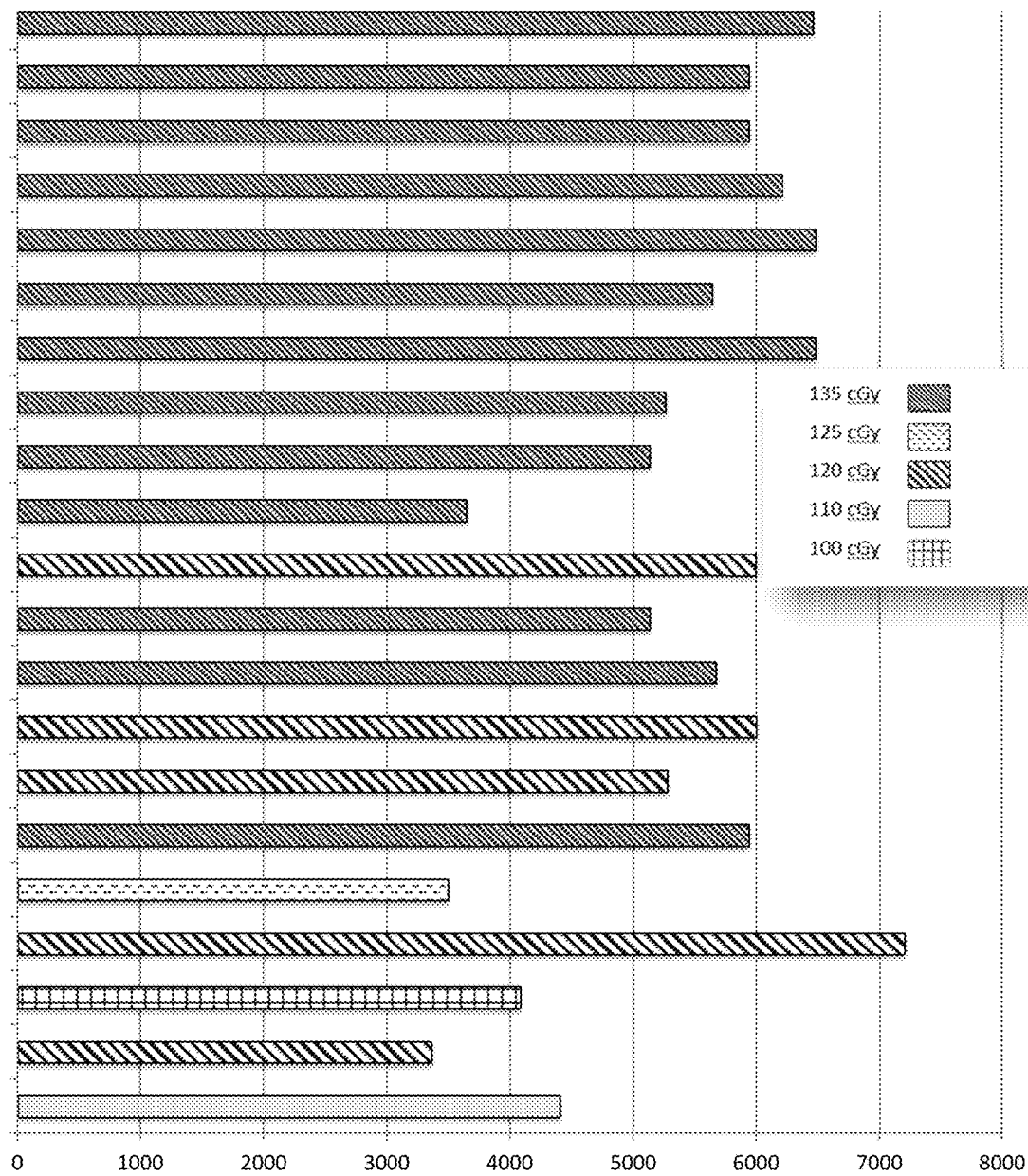
FIG. 56 shows total dose versus dose per fraction given twice-daily for locally advanced disease, as well as macroscopic metastatic disease.

FIG. 56 compares total dose versus dose per fraction given twice-daily for locally advanced disease, as well as macroscopic metastatic disease. Again, although there is 100% complete/continued regression, the wide variance in total dose used still requires further elucidation to determine its optimum range as to total dose (cGy), for locally advanced/macroscopic metastatic disease.

Figure 57:
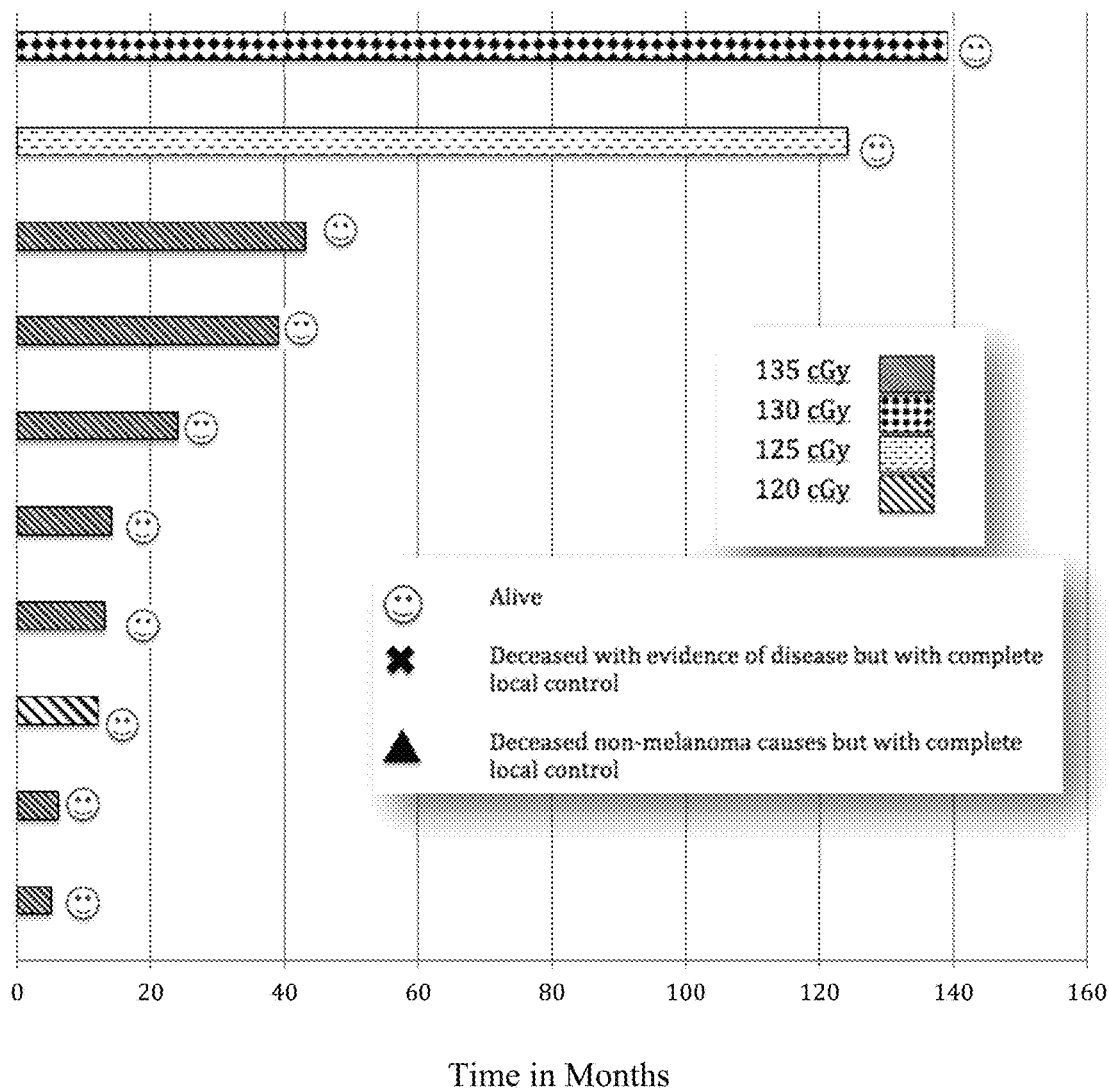
FIGS. 57 and 58 illustrate post-operative microscopic disease over time.
Figure 58:
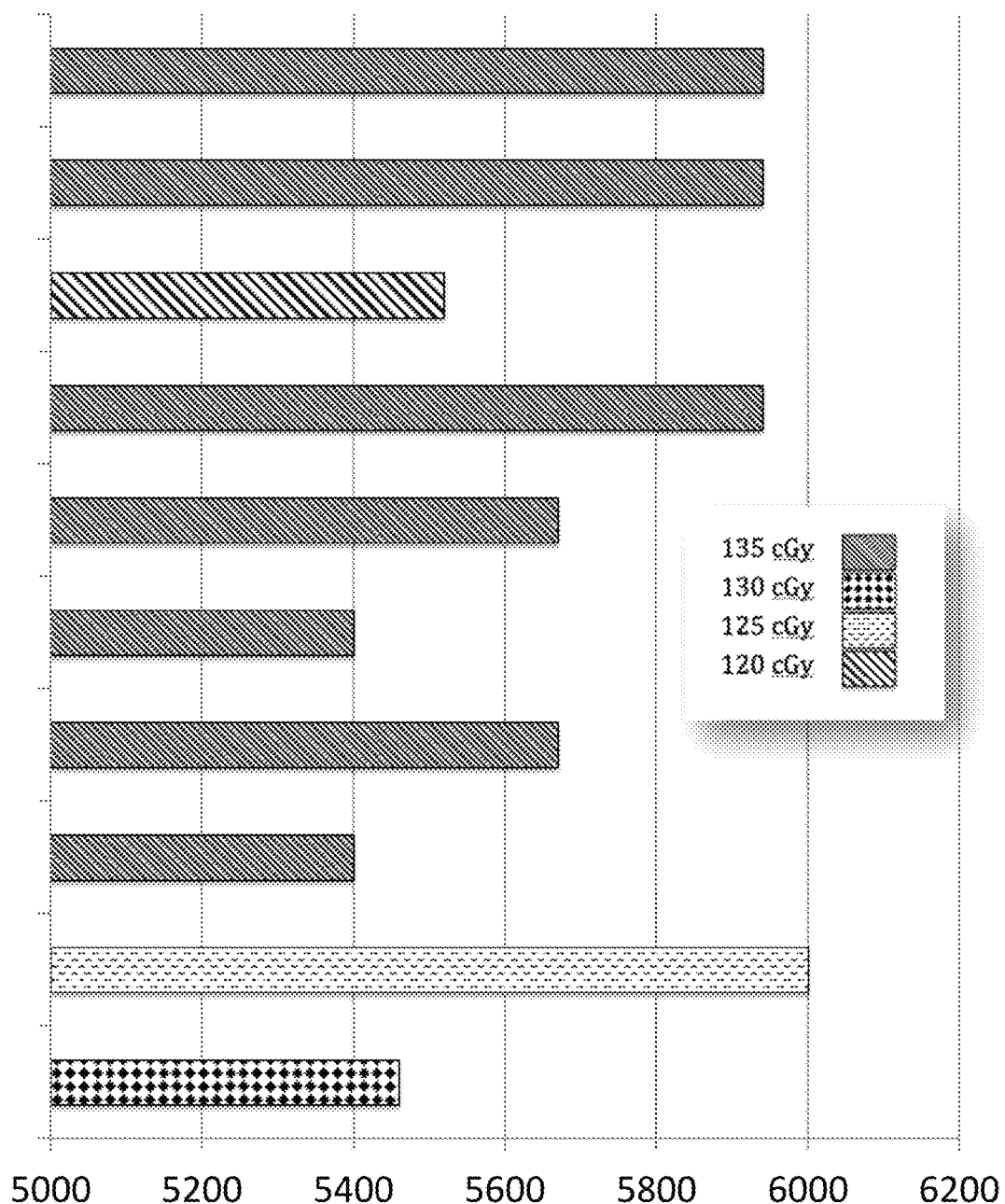
Figure 59:
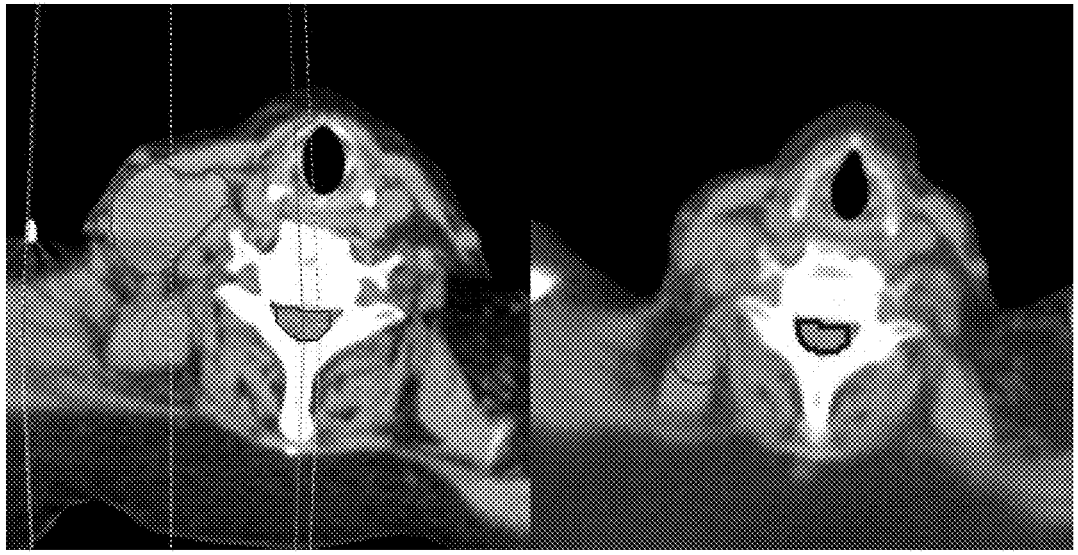
FIGS. 59-63 are serial "slices" comparing the original mass (left) with the post-treatment response (right) for the patient of Example 3.
Figure 60:
Figure 61:
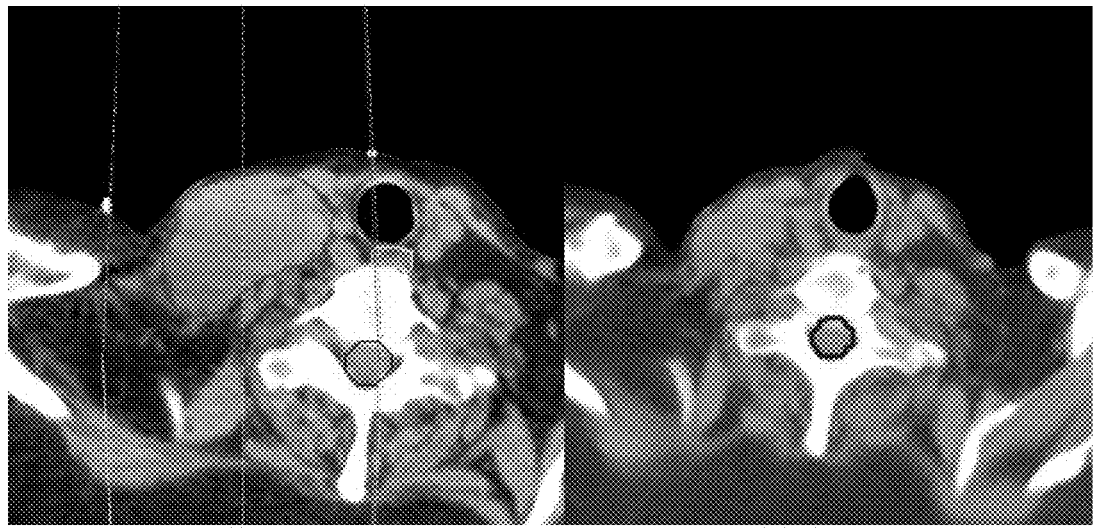
Figure 62:
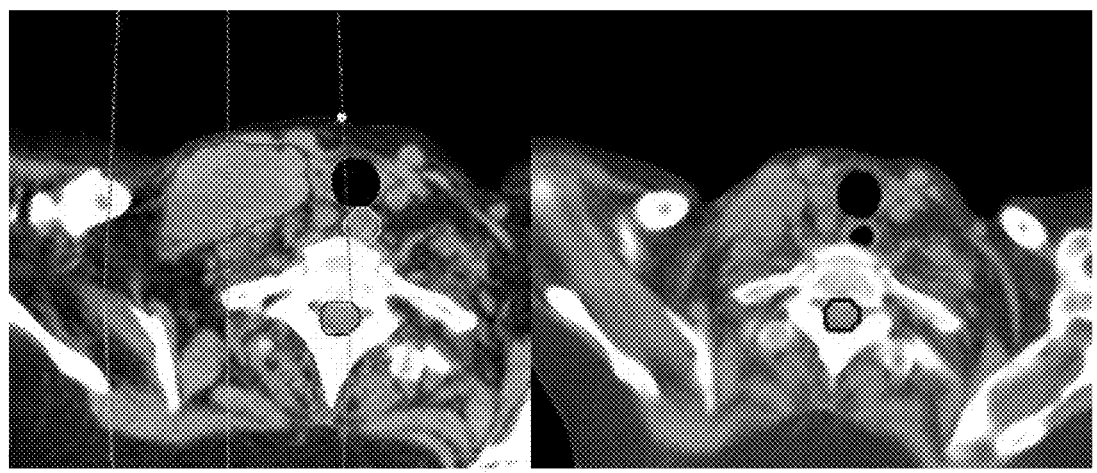
Figure 63:

FIGS. 57 and 58 illustrate post-operative microscopic disease over time. These patients are included for totality, and document a 100% local/regional control. When one compares the standard once-daily radiation therapy in the postoperative setting for microscopic disease, the medical literature would indicate one cannot achieve 100% local/regional control. Our data would indicate we have achieved that goal. FIG. 57 illustrates disease control using dose per fraction. FIG. 58 illustrates the total dose delivered (in cGy).

Data Observations

As we review the data for twice-daily radiation therapy in this patient population, striking contrasts surface when comparing the historical treatment of melanoma itself, as well as with non-melanoma malignancies. The range of doses utilized for this select twice-daily patient series extends from an initial 135 cGy per fraction to 100 cGy per fraction. The accompanying visual examples in this patient population demonstrate the sensitivity to twice-daily treatment for malignant melanoma that is diametrically different compared to the same malignancy treated once-daily.

Just as importantly, one must now question the ideal total dose required to obtain optimum control of disease. Several factors are evident in our data. The first is that the total dose required to achieve local/regional control has no comparison to cancers that are not malignant melanoma. Thus one cannot use studies involving carcinomas or sarcomas to extrapolate their data, since the biologic response is dissimilar. It is evident that the sensitivity of malignant melanoma cells goes from radio resistant at standard once-daily doses to marked sensitivity with twice-daily, potentially allowing a reduction in total dose requirement. Respecting the historical tolerance of normal tissue protects the patient as to the upper safe limit used, but we do not know yet the lower limit; in essence, the patient avoids side effects, with more safety beyond what is presently experienced.

Next, the sensitivity of malignant melanoma cells to twice-daily radiation may also change the requirements for continuous delivery when compared with other malignancies. In fact, interruption of greater than five weeks during treatment for a 94-year-old female did not initially affect local control of her disease.

The last observation involves the time from the initiation of treatment until there is disappearance of tumors when a second unrelated area of disease requires treatment. For example, if a new area of metastatic disease (or a new area of involvement unrelated to the original malignancy) occurs following completion of a course of therapy, there appears to be a much more rapid therapeutic response with further treatment. This observation speaks in favor of an immunotherapeutic component to the elimination of disease. Rather than weeks/months, visible response is evident in a matter of days. This was the case for the patient of Example #3, who recently developed a metastatic right neck mass. Multiple daily "black out" episodes occurred, risking injury due to extrinsic compression of the vasculature. Physical examination revealed a rock-hard mass in the right lower neck, firmly fixed to the underlying muscle and bone. FIGS. 59-63 are serial "slices" comparing the original mass (left) with the post-treatment response (right). Within three treatment days (6 fractions at 125 cGy per fraction), the mass was reduced by 70%. By day 5, the mass was no longer physically palpable. Now evident on CT scans are only the normal structures of the neck. No immunotherapy was administered, and no further blackouts have occurred.

Certain aspects of the radiation therapy provided in this disclosure include a specific dose of radiation per-fraction administered at the time of each treatment, a specific time interval for the actual treatment delivery of two, and up to seven, treatments per day, and a specific total dose of radiation delivered for the entire treatment sequence. Each of these components has variable criteria based upon the size and volume of disease, its location(s), the multiple nature of the malignant deposits to be safely treated, the tolerance of tissue within those locations, the biologic effect of how twice/multiple-daily radiation affects malignant melanoma cells and the total dose of radiation to be administered.

The treatment regimen provided in these examples provide several beneficial results, for example: A) a seismic response in regression and/or disappearance of the treated tumor mass(es), B) ultimate local/regional control of malignant melanoma, C) markedly increased patient survival, D) an immuno-therapeutic component for the treatment's success without the use of pharmaceutical agents. These benefits ultimately offer a statistical cure which has never been documented for this uniformly fatal malignancy while protecting uninvolved normal but exposed tissue/organs.

Without being bound to theory, it is believed that the radiation protocols described herein provide a dramatic change in the body's immune response. Specifically, the occurrence of metastatic disease has been altered and reduced. With this treatment regimen, the body's own immune response is activated. The structure of these immune compounds created by this treatment schedule are undefined as of yet, however, must be produced by the human body itself. Thus, the evolution of these chemicals and/or compounds, produced as a result of the uniqueness of this radiation delivery schedule, occurs in, and is regulated by, the patient's body. The exactness of the production of these chemicals and/or compounds is specific to each genetic tumor profile located within a specific patient.

The present medical literature would indicate a complete response from immunotherapeutic drugs to be, at best, 4-13%, with the higher number corresponding to those malignancies with a BRAF mutation. Oddly, 13% of patients in the immunotherapeutic drug studies withdrew because of unacceptable adverse side effects. In contrast, for radiation, 95% complete response within the treated region is obtained. In addition, no one who received the twice-daily radiation regimen discontinued treatment because of side effects.

With immunotherapeutic drugs, 50% of patients demonstrate progression of disease by six months, with most patients progressing with disease by 14 months. In essence, immunotherapy offers a temporary "standoff" and no potential for cure from disease. With the protocol described herein for radiation delivery, the majority of patients document no signs of progression of disease and are potentially cured. As the exact dosing schedule continues to constantly evolve, the patients treated according to the protocols described herein extend for greater than two decades following treatment, with many patients demonstrating no evidence of further disease. Again, those who do demonstrate further disease can still be treated, since no resistance has developed, as routinely occurs with pharmaceutical agents.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

I claim:

1. A method for treating cutaneous malignant melanoma in a subject comprising irradiating cutaneous malignant melanoma on the skin of the subject with at least two fractions of radiation per day, said fractions of radiation being selected from about 100 centiGray (cGy) or about 135 centiGray (cGy) and said fractions being separated by a time interval of at least about 0.5 hour.

2. The method according to claim 1, said method comprising irradiating said cutaneous malignant melanoma on the skin of the subject with at least two fractions of radiation per day, said fractions of radiation being about 100 centiGray (cGy) and said fractions being separated by a time interval of at least about 0.5 hour.

3. The method according to claim 1, said method comprising irradiating cutaneous malignant melanoma on the skin of the subject with at least two fractions of radiation per day, said fractions of radiation being about 135 centiGray (cGy) and said fractions being separated by a time interval of at least about 0.5 hour.

4. The method according to claim 1, wherein the fractions of radiation are separated by a time interval ranging between about 1 hour and, maximally, about 23 hours.

5. The method according to claim 1, wherein the fractions of radiation are separated by a time interval ranging between about 1 hour and about 8 hours.

6. The method according to claim 1, wherein the fractions of radiation are separated by a time interval ranging between about 2 hours and about 8 hours.

7. The method according to claim 1, wherein the fractions of radiation are separated by a time interval ranging between about 1 hour and about 6 hours.

8. The method according to claim 1, said method comprising treating said subject with radiation and a therapy comprising surgery, chemotherapy, targeted immunotherapy, immunotherapy or a combination of said therapies.

9. The method according to claim 8, wherein said chemotherapy, targeted immunotherapy or immunotherapy is selected from treatment with vemurafenib, dabrafenib, trametinib, cobimetinib, temozolomide, dacarbazine, paclitaxel or combinations thereof.

10. The method according to claim 9, wherein said subject is treated with a total of between 20 and 100 fractions of radiation.

11. The method according to claim 10, wherein said subject is treated with a total of between 20 and 56 fractions of radiation.

12. The method according to claim 8, wherein said chemotherapy, targeted immunotherapy or immunotherapy is selected from treatment with pembrolizumab, ipilmumab, nivolumab, interferon alpha, interferon alpha 2b or combinations thereof.

13. The method according to claim 12, wherein said subject is treated with a total of between 20 and 100 fractions of radiation.

14. The method according to claim 13, wherein said subject is treated with a total of between 20 and 56 fractions of radiation.

15. The method according to claim 8, wherein said subject is treated with a total of between 20 and 100 fractions of radiation.

16. The method according to claim 15, wherein said subject is treated with a total of between 20 and 56 fractions of radiation.

17. The method according to claim 1, wherein said subject is treated with a total of between 20 and 100 fractions of radiation.

18. The method according to claim 17, wherein said subject is treated with a total of between 20 and 56 fractions of radiation.

19. The method according to claim 1, said method comprising irradiating said cutaneous malignant melanoma on the skin of the subject with at least two fractions of radiation per day, said fractions of radiation being about 100 centiGray (cGy) and said fractions being separated by a time interval of at least about 1 hour.

* * * * *

UNITED STATES PATENT AND TRADEMARK OFFICE
CERTIFICATE OF CORRECTION

Page 1 of 1

PATENT NO. : 10,426,972 B2
APPLICATION NO. : 15/864178
DATED : October 1, 2019
INVENTOR(S) : Norman H. Anderson It is certified that error appears in the above-identified patent and that said Letters Patent is hereby corrected as shown below:

In the Specification

Column 5,
Line 40, "repeat MM" should read --repeat MRI--.

Column 10,
Line 30, "repeat Mill" should read --repeat MRI--.

Signed and Sealed this
Twelfth Day of May, 2020

Andrei Iancu
*Director of the United States Patent and Trademark Office*